（12）United States Patent
Lim et al.

(10) Patent No.: US 7,420,060 B2
(45) Date of Patent: Sep. 2, 2008

(54) BENZOPYRAN DERIVATIVES SUBSTITUTED WITH A THIOXOBENZOXAZOLE DERIVATIVE, PHARMACEUTICALLY ACCEPTABLE SALTS THEREOF, THEIR PREPARATIONS AND PHARMACEUTICAL COMPOSITIONS CONTAINING THEM

(75) Inventors: Hong Lim, Seoul (KR); Dong Ha Lee, Taejon-si (KR); Sun Ok Kim, Taejon-si (KR); Sung-Eun Yoo, Kongju-si (KR); Kyu Yang Yi, Taejon-si (KR); Sun Kyung Lee, Taejon-si (KR); Jee Hee Suh, Taejon-si (KR); Nak Jeong Kim, Taejon-si (KR); Sun Kyung Hwang, Taejon-si (KR); Tae Mi Kim, Taejon-si (KR); Byung Ho Lee, Taejon-si (KR); Ho-Won Seo, Taejon-si (KR)

(73) Assignee: Schaeffler KG (DE)

( * ) Notice: Subject to any disclaimer, the term of this patent is extended or adjusted under 35 U.S.C. 154(b) by 0 days.

(21) Appl. No.: 10/558,111

(22) PCT Filed: May 28, 2004

(86) PCT No.: PCT/KR2004/001271

§ 371 (c)(1),
(2), (4) Date: Oct. 25, 2006

(87) PCT Pub. No.: WO2004/106331

PCT Pub. Date: Dec. 9, 2004

(65) Prior Publication Data

US 2007/0093481 A1    Apr. 26, 2007

(30) Foreign Application Priority Data

May 28, 2003  (KR)  ................. 10-2003-0034110

(51) Int. Cl.
*C07D 263/58* (2006.01)
(52) U.S. Cl. ..................................... 548/221
(58) Field of Classification Search .................. 548/221
See application file for complete search history.

(56) References Cited

OTHER PUBLICATIONS

Parker, J. Angina Pectoris: A Review of Current and Emerging Therapies. The American Journal of Managed Care, 2004, 10, S332-S338.*
Vilas-Boas, et al. Current Insights into the Modern Treatment of Decompensated Heart Failure. 2006, 87, 329-337.*
Thrombolytic therapy [online].[retrieved on Nov. 19, 2007]. Retrieved from the Internet, URL; http://www.nlm.nih.gov/medlineplus/ency/article/007089.htm>.*
RN 94544-88-4, CAPLUS retrieved on Jun, 10, 2008.*
Gary J. Grover, Pharmacology of ATP-Sensitive Potassium Channel . . . , Can. J. Physiol. Pharmacol., vol. 75, pp. 309-315 (1997).
Gary D. Lopaschuk, et al, Manipulation of Energy Metabolism in the Heart, Science & Medicine, pp. 42-51, ((1997).
A.A. Starkov, "Mild" Uncoupling of Mitochondria, Bioscience Reports. vol. 17, No. 3, pp. 273-279, (1997).
Skulachev, Vladimir P., et al., Role of Uncoupled and Non-Coupled Oxidations in Maintenance . . . , Quarterly Reviews of Biophysics, vol. 29, pp. 169-202, (1996).
Okubo, Shinji, et al., Myocardial Preconditioning: Basic . . . , Molecular and Cellular Biochemistry, vol. 196, pp. 3-12, (1999).
Moreau, Jean-Luc, et al., Central Adenosine A . . . , Brain Research Reviews, vol. 31, pp. 65-82, (1999).

* cited by examiner

*Primary Examiner*—Rebecca L Anderson
*Assistant Examiner*—Shawquia Young
(74) *Attorney, Agent, or Firm*—Lucas & Mercanti, LLP

(57) ABSTRACT

The present invention relates to benzopyran derivatives substituted with a thioxobenzoxazole derivative, or pharmaceutically acceptable salts thereof, processes for preparing the same and a pharmaceutical composition containing the above as an effective ingredient Benzopyran derivatives substituted with thioxobenzoxazole derivatives, represented in <Formula 1>, have the function of protecting heart from ischemia-reperfusion both in vivo and in vitro, so that a pharmaceutical composition containing benzopyran derivatives substituted with thioxobenzoxoazole derivatives or pharmaceutically acceptable salts thereof of the present invention as an effective ingredient can be effectively used for the protection of tissues influenced by ischemia-reperfusion, for example, for the protection of heart, nervous cells, brain, retinal cells, storage organs, etc, and for the treatment of diseases caused by ischemia-reperfusion.

4 Claims, No Drawings

BENZOPYRAN DERIVATIVES SUBSTITUTED WITH A THIOXOBENZOXAZOLE DERIVATIVE, PHARMACEUTICALLY ACCEPTABLE SALTS THEREOF, THEIR PREPARATIONS AND PHARMACEUTICAL COMPOSITIONS CONTAINING THEM

This patent application claims the benefit of priority from Korean Patent Application No. 10-2003-0034110 filed May 28, 2003 through PCT Application Serial No. PCT/KR2004/001271 filed May 28, 2004 the contents of which are incorporated herein by reference.

FIELD OF THE INVENTION

The present invention relates to benzopyran derivatives substituted with a thioxobenzoxazole derivative, represented in <Formula 1>, pharmaceutically acceptable salts thereof, processes for preparing the same and pharmaceutical compositions containing them as an effective ingredient.

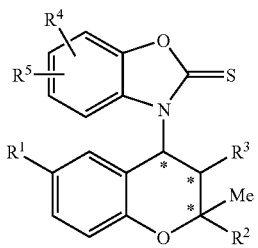

<Formula 1>

(Wherein, $R^1$, $R^2$, $R^3$, $R^4$, $R^5$ and * are as defined in the description.)

BACKGROUND

Ischemic heart disease results from myocardial ischemia developed by a serious deficiency of oxygen supply caused by interruption of blood flow to heart by a reason like arteriosclerosis (G. J. Grover, *Can. J. Physiol.* 75, 309, 1997; G. D. Lopaschuk et al. *Science & Medicine* 42, 1997). Myocardial ischemia induces pathological changes in cells progressively, leading to irreversible myocardial damage and even necrosis of cells and tissues, at last. In early stage when damage is reversible, irreversible damage might be prevented by reperfusion through surgical operations such as PTCA (percutaneous transluminal coronary angioplasty) and CABG (coronary artery bypass graft) or using thrombolytics, but the restoration of flow by reperfusion therapy is accompanied by a further injurious phenomenon called reperfusion injury (D. J. Hearse, *Medicographia* 18, 22, 1996). It is difficult to clearly separate ischemic injury from that mediated by reperfusion. Reperfusion injury is caused by sudden restoration of blood flow by reperfusion therapy, mainly due to reactive oxygen free radicals and calcium overload. Reperfusion injury includes a range of events, such as arrhythmia, vascular damage, myocardial dysfunction and serious neurocognitive dysfunction.

In order to delay damage by ischemia and minimize reperfusion injury, studies have actively been undergoing on pharmacotherapy using immune modulators, agents to suppress apoptosis, ion channel modulators, etc, artificial blood products to enhance the oxygen carrying potential of blood, and development of devices and operation procedures, but neither of them has been in commercial use, so far. As an ion channel modulators, an inhibitor of Na—H exchanger (NHE), an adenosine $A_1/A_2$ antagonist and a $K_{ATP}$ opener (ATP-sensitive potassium channel opener) draw our attention.

According to earlier reports, diazoxide, a $K_{ATP}$ opener, can reduce damage due to oxidative stress by suppressing the generation of oxygen free radicals in mitochondria by inducing oxidation of flavoprotein (A. A. Starkov, *Biosci, Rep.* 17, 273, 1997; V. P. Skulachev, *Q. Rev. Biophus.* 29, 169, 1996), and the opening of $K_{ATP}$ relates to the generation of antioxidant enzymes (S. Okubo et al., *Mol. and cell Biochem,* 196, 3, 1999) and the decrease of release of excitatory amino acids (J-L Moreau, G. Huber, *Brain Res.,* 31, 65, 1999). $K_{ATP}$, found first in myocardium, is widely distributed in many organs and tissues, for example, beta-cells of pancreas, smooth muscle, kidney and central nervous system, so that it has been a major target for the development of a novel medicine. Atwal et al have reported that benzopyranyl cyanoguanidines (BMS-180448) having a structure represented in the below <Formula 2> opens $K_{ATP}$ selectively, meaning that it might have cardioprotective function, which provides a chance to develop a novel therapeutic agent for ischemic heart diseases.

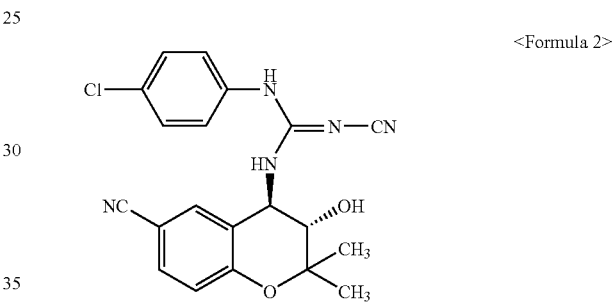

<Formula 2>

Thus, the inventors of present invention synthesized benzopyran derivatives substituted with a thioxobenzoxazole derivative, in which the guanidinyl group substituted in the 4-position of benzopyran was cyclized to a benzene ring, aniline nitrogen was changed into oxygen to form a benzoxazole ring and N-cyano group was changed into thioxo group. And the present inventors completed this invention by confirming that the compound of the invention had an excellent cardioprotective effect against damage by ischemia-reperfusion, so that it could be effectively used as a protective agent or therapeutic agent for ischemia-reperfusion related diseases. Precisely, the compound can be used for the treatment of ischemic heart diseases such as myocardial infarction, unstable angina pectoris, the protection of heart upon thrombolytic therapy or reperfusion therapy such as PTCA (percutaneous transluminal coronary angioplasty) and CABG (coronary artery bypass graft), and the protection of ischemia-reperfusion related tissues such as nerve cells, brain, retinal cells, storage organs, etc.

SUMMARY OF THE INVENTION

It is an object of this invention to provide benzopyran derivatives substituted with a thioxobenzoxazole derivative, represented in <Formula 1>, or pharmaceutically acceptable salts thereof.

It is also an object of this invention to provide preparation processes for benzopyran derivatives substituted with a thioxobenzoxazole derivative, represented in <Formula 1>, or pharmaceutically acceptable salts thereof.

It is a further object of this invention to provide a pharmaceutical composition containing benzopyran derivatives substituted with a thioxobenzoxazole derivative, represented in <Formula 1>, or pharmaceutically acceptable salts of the same as an effective ingredient.

DETAILED DESCRIPTION OF PREFERRED EMBODIMENTS

In order to achieve the above object, the present invention provides benzopyran derivatives substituted with a thioxobenzoxazole derivative, pharmaceutically acceptable salts thereof, processes for preparing the same and a pharmaceutical composition containing the above as an effective ingredient.

Hereinafter, the present invention is described in detail.

The present invention provides benzopyran derivatives substituted with a thioxobenzoxazole derivative, represented in <Formula 1>, or pharmaceutically acceptable salts thereof.

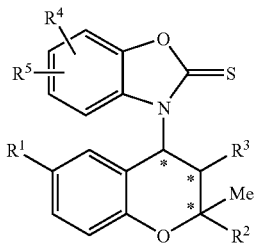

<Formula 1>

(Wherein, $R^1$ is $NO_2$, $NH_2$, H, CN, $NHCOCH_3$, NHCOPh, $NHCOCF_3$ or $NHSO_2CH_3$;

$R^2$ is

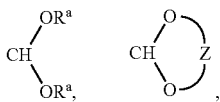

$CH_2OR^a$, $CO_2R^a$ or $R^a$

Wherein, $R^a$ is $C_1$~$C_4$ straight or branched alkyl;

Z is $C_2$~$C_6$ straight or branched alkyl;

$R^3$ is OH or $OCOCH_3$;

$R^4$ and $R^5$ are independently H, $C_1$~$C_4$ straight or branched alkyl, Cl, Br, F, $NO_2$, OMe, $CO_2Me$ or $CF_3$;

* represents a chiral carbon.)

The present invention also provides, in addition to benzopyran derivatives represented in <Formula 1> and pharmaceutically acceptable salts, solvates, and hydrates thereof.

Benzopyran derivatives of the present invention represented in <Formula 1> include not only a racemic mixture but also any diastereoisomer in which at least one carbon in the 2, 3, or 4-positon is chiral. In the above <Formula 1>, if all the carbons of 2, 3 and 4-position are chiral, 3,4-dihydro benzopyran compounds of the present invention are in the form of diastereoisomers as seen in ($I_1$), ($I_2$), ($I_3$), and ($I_4$) in the below <Formula 3>.

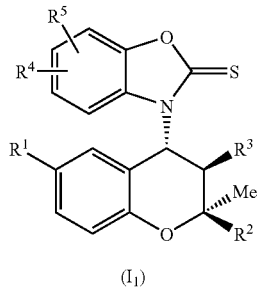

($I_1$)

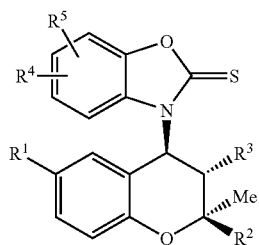

($I_2$)

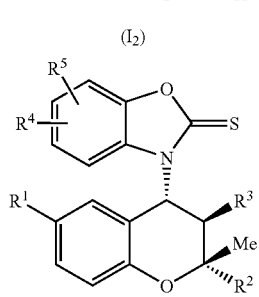

($I_3$)

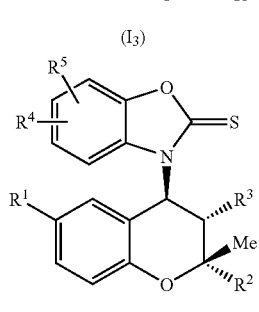

($I_4$)

<Formula 3>

(Wherein, $R^1$, $R^2$, $R^3$, $R^4$, and $R^5$ are as defined in <Formula 1>.)

Preferably, the compounds of <Formula 1> include:

1) (2R,3R,4S)-6-nitro-3,4-dihydro-3-hydroxy-2-dimethoxymethyl-2-methyl-4-(2-thioxobenzoxazol-3-yl)-2H-1-benzopyran;

2) (2R,3S,4R)-6-nitro-3,4-dihydro-3-hydroxy-2-dimethoxymethyl-2-methyl-4-(2-thioxobenzoxazol-3-yl)-2H-1-benzopyran;

3) (2S,3R,4S)-6-nitro-3,4-dihydro-3-hydroxy-2-dimethoxymethyl-2-methyl-4-(2-thioxobenzoxazol-3-yl)-2H-1-benzopyran;

4) (2S,3S,4R)-6-nitro-3,4-dihydro-3-hydroxy-2-dimethoxymethyl-2-methyl-4-(2-thioxobenzoxazol-3-yl)-2H-1-benzopyran;

5) (2R,3R,4S)-6-nitro-3,4-dihydro-3-hydroxy-2-dimethoxymethyl-2-methyl-4-(6-methyl-2-thioxobenzoxazol-3-yl)-2H-1-benzopyran;

6) (2R,3R,4S)-6-nitro-3,4-dihydro-3-hydroxy-2-dimethoxymethyl-2-methyl-4-(4-methyl-2-thioxobenzoxazol-3-yl)-2H-1-benzopyran;
7) (2R,3R,4S)-6-nitro-3,4-dihydro-3-hydroxy-2-dimethoxymethyl-2-methyl-4-(5-chloro-2-thioxobenzoxazol-3-yl)-2H-1-benzopyran;
8) (2R,3R,4S)-6-nitro-3,4-dihydro-3-hydroxy-2-dimethoxymethyl-2-methyl-4-(5-methyl-2-thioxobenzoxazol-3-yl)-2H-1-benzopyran;
9) (2R,3R,4S)-6-nitro-3,4-dihydro-3-hydroxy-2-dimethoxymethyl-2-methyl-4-(6-nitro-2-thioxobenzoxazole-3-yl)-2H-1-benzopyran;
10) (2R,3R,4S)-6-nitro-3,4-dihydro-3-hydroxy-2-dimethoxymethyl-2-methyl-4-(5-methoxy-2-thioxobenzoxazol-3-yl)-2H-1-benzopyran;
11) (2R,3R,4S)-6-nitro-3,4-dihydro-3-hydroxy-2-dimethoxymethyl-2-methyl-4-(5-bromo-2-thioxobenzoxazol-3-yl)-2H-1-benzopyran;
12) (2R,3R,4S)-6-nitro-3,4-dihydro-3-hydroxy-2-dimethoxymethyl-2-methyl-4-(5-t-butoxy-2-thioxobenzoxazol-3-yl)-2H-1-benzopyran;
13) (2R,3R,4S)-6-nitro-3,4-dihydro-3-hydroxy-2-dimethoxymethyl-2-methyl-4-(6-fluoro-2-thioxobenzoxazol-3-yl)-2H-1-benzopyran;
14) (2R,3R,4S)-6-nitro-3,4-dihydro-3-hydroxy-2-dimethoxymethyl-2-methyl-4-(4-methoxycarbonyl-2-thioxobenzoxazol-3-yl)-2H-1-benzopyran;
15) (2R,3R,4S)-6-nitro-3,4-dihydro-3-hydroxy-2-dimethoxymethyl-2-methyl-4-(5-methoxycarbonyl-2-thioxobenzoxazol-3-yl)-2H-1-benzopyran;
16) (2R,3R,4S)-6-nitro-3,4-dihydro-3-hydroxy-2-dimethoxymethyl-2-methyl-4-(5-trifluoromethyl-2-thioxobenzoxazol-3-yl)-2H-1-benzopyran;
17) (2R,3R,4S)-6-amino-3,4-dihydro-3-hydroxy-2-dimethoxymethyl-2-methyl-4-(2-thioxobenzoxazol-3-yl)-2H-1-benzopyran;
18) (2S,3S,4R)-6-amino-3,4-dihydro-3-hydroxy-2-dimethoxymethyl-2-methyl-4-(2-thioxobenzoxazol-3-yl)-2H-1-benzopyran;
19) (2S,3R,4S)-6-amino-3,4-dihydro-3-hydroxy-2-dimethoxymethyl-2-methyl-4-(2-thioxobenzoxazol-3-yl)-2H-1-benzopyran;
20) (2R,3S,4R)-6-amino-3,4-dihydro-3-hydroxy-2-dimethoxymethyl-2-methyl-4-(2-thioxobenzoxazol-3-yl)-2H-1-benzopyran;
21) (2R,3R,4S)-6-amino-3,4-dihydro-3-hydroxy-2-dimethoxymethyl-2-methyl-4-(6-methyl-2-thioxobenzoxazol-3-yl)-2H-1-benzopyran;
22) (2R,3R,4S)-6-amino-3,4-dihydro-3-hydroxy-2-dimethoxymethyl-2-methyl-4-(5-methyl-2-thioxobenzoxazol-3-yl)-2H-1-benzopyran;
23) (2R,3R,4S)-6-amino-3,4-dihydro-3-hydroxy-2-dimethoxymethyl-2-methyl-4-(4-methyl-2-thioxobenzoxazol-3-yl)-2H-1-benzopyran;
24) (2R,3R,4S)-6-amino-3,4-dihydro-3-hydroxy-2-dimethoxymethyl-2-methyl-4-(5-chloro-2-thioxobenzoxazol-3-yl)-2H-1-benzopyran;
25) (2R,3R,4S)-6-amino-3,4-dihydro-3-hydroxy-2-dimethoxymethyl-2-methyl-4-(5-methoxy-2-thioxobenzoxazol-3-yl)-2H-1-benzopyran;
26) (2R,3R,4S)-6-amino-3,4-dihydro-3-hydroxy-2-dimethoxymethyl-2-methyl-4-(5-t-butoxy-2-thioxobenzoxazol-3-yl)-2H-1-benzopyran;
27) (2R,3R,4S)-6-amino-3,4-dihydro-3-hydroxy-2-dimethoxymethyl-2-methyl-4-(6-fluoro-2-thioxobenzoxazol-3-yl)-2H-1-benzopyran;
28) (2R,3R,4S)-6-amino-3,4-dihydro-3-hydroxy-2-dimethoxymethyl-2-methyl-4-(5-methoxycarbonyl-2-thioxobenzoxazol-3-yl)-2H-1-benzopyran;
29) (2R,3R,4S)-6-amino-3,4-dihydro-3-hydroxy-2-dimethoxymethyl-2-methyl-4-(4-methoxycarbonyl-2-thioxobenzoxazol-3-yl)-2H-1-benzopyran;
30) (2R,3R,4S)-6-amino-3,4-dihydro-3-hydroxy-2-dimethoxymethyl-2-methyl-4-(5-trifluoromethyl-2-thioxobenzoxazol-3-yl)-2H-1-benzopyran;
31) (2R,3R,4S)-6-nitro-3,4-dihydro-3-acetoxy-2-dimethoxymethyl-2-methyl-4-(2-thioxobenzoxazol-3-yl)-2H-1-benzopyran;
32) (2R,3R,4S)-6-amino-3,4-dihydro-3-acetoxy-2-dimethoxymethyl-2-methyl-4-(2-thioxobenzoxazol-3-yl)-2H-1-benzopyran;
33) (2R,3R,4S)-6-acetylamino-3,4-dihydro-3-hydroxy-2-dimethoxymethyl-2-methyl-4-(2-thioxobenzoxazol-3-yl)-2H-1-benzopyran;
34) (2R,3R,4S)-6-acetylamino-3,4-dihydro-3-acetoxy-2-dimethoxymethyl-2-methyl-4-(2-thioxobenzoxazol-3-yl)-2H-1-benzopyran;
35) (2R,3R,4S)-6-benzoylamino-3,4-dihydro-3-hydroxy-2-dimethoxymethyl-2-methyl-4-(2-thioxobenzoxazol-3-yl)-2H-1-benzopyran;
36) (2R,3R,4S)-6-trifluoroacetylamino-3,4-dihydro-3-hydroxy-2-dimethoxymethyl-2-methyl-4-(2-thioxobenzoxazol-3-yl)-2H-1-benzopyran;
37) (2R,3R,4S)-6-methanesulfonylamino-3,4-dihydro-3-hydroxy-2-dimethoxymethyl-2-methyl-4-(2-thioxobenzoxazol-3-yl)-2H-1-benzopyran;
38) (2R,3R,4S)-6-nitro-3,4-dihydro-3-hydroxy-2-methoxymethyl-2-methyl-4-(2-thioxobenzoxazol-3-yl)-2H-1-benzopyran;
39) (2R,3R,4S)-6-nitro-3,4-dihydro-3-hydroxy-2-methoxymethyl-2-methyl-4-(5-chloro-2-thioxobenzoxazol-3-yl)-2H-1-benzopyran;
40) (2R,3R,4S)-6-nitro-3,4-dihydro-3-hydroxy-2-methoxycarbonyl-2-methyl-4-(2-thioxobenzoxazol-3-yl)-2H-1-benzopyran;
41) (2R,3R,4S)-6-nitro-3,4-dihydro-3-hydroxy-2-methoxycarbonyl-2-methyl-4-(5-chloro-2-thioxobenzoxazol-3-yl)-2H-1-benzopyran;
42) (2R,3R,4S)-6-nitro-3,4-dihydro-3-hydroxy-2-([1,3]dioxolan-2-yl)-2-methyl-4-(2-thioxobenzoxazol-3-yl)-2H-1-benzopyran;
43) (2R,3R,4S)-6-nitro-3,4-dihydro-3-hydroxy-2-([1,3]dioxan-2-yl)-2-methyl-4-(2-thioxobenzoxazol-3-yl)-2H-1-benzopyran;
44) (2R,3R,4S)-6-nitro-3,4-dihydro-3-hydroxy-2-diethoxymethyl-2-methyl-4-(2-thioxobenzoxazol-3-yl)-2H-1-benzopyran;
45) (2R,3S,4R)-6-nitro-3,4-dihydro-3-hydroxy-2-diethoxymethyl-2-methyl-4-(2-thioxobenzoxazol-3-yl)-2H-1-benzopyran;
46) (2S,3R,4S)-6-nitro-3,4-dihydro-3-hydroxy-2-diethoxymethyl-2-methyl-4-(2-thioxobenzoxazol-3-yl)-2H-1-benzopyran;
47) (2S,3S,4R)-6-nitro-3,4-dihydro-3-hydroxy-2-diethoxymethyl-2-methyl-4-(2-thioxobenzoxazol-3-yl)-2H-1-benzopyran; and
48) (2S,3R,4S)-6-amino-3,4-dihydro-3-hydroxy-2-diethoxymethyl-2-methyl-4-(2-thioxobenzoxazol-3-yl)-2H-1-benzopyran.

The compounds of the above <Formula 1> of the present invention are available in the form of pharmaceutically acceptable salts, and acid addition salts prepared by pharmaceutically acceptable free acids or metal salts are useful.

The acid salts of the compounds according to the present invention can be prepared in the customary manner, for example by dissolving the compound of <Formula 1> in excess aqueous acid solution and precipitating the salt using a water-miscible organic solvent, such as methanol, ethanol, acetone or acetonitrile. It is also possible to prepare the acid salt by heating equivalent amounts of the compound of <Formula 1> and an acid in water or alcohol, such as glycol monomethyl ether, and then evaporating the mixture to dryness or filtering off the precipitated salt with suction. Whether it is inorganic or organic, a free acid can be used if it is pharmaceutically acceptable. Examples of the inorganic free acid include hydrochloric acid, hydrobromic acid, sulfuric acid, and phosphoric acid. Available organic free acids are exemplified by citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid and aspartic acid.

Also, the compounds of <Formula 1> may be in the form of pharmaceutically acceptable alkali metal or alkaline earth metal salts. The alkali metal or alkaline earth metal salts of the compounds of <Formula 1> can be obtained, for example, by dissolving the compound of <Formula 1> in excess alkali metal or alkaline earth metal hydroxide solution, filtering off the undissolved materials and evaporating the filtrate to dryness. Sodium, potassium or calcium salts are pharmaceutically suitable.

The present invention also provides processes for preparing benzopyran derivatives substituted with a thioxobenzoxazole derivative, represented in <Formula 1>.

Particularly, the present invention provides a process for preparing a compound of Formula (I). As shown in <Scheme 1>, Reaction of an epoxide compound (III) with a 2-aminophenol compound (IV) in the presence of a proper metal salt gives a compound of Formula (V). Then, cyclization of compound (V) using an appropriate thiocarbonyl transfer reagent, affords a 2-thioxobenzoxazole compound (I'). Finally, benzopyran compound of Formula (I) can be prepared by changing substituents $R^1$, $R^2$, $R^3$, $R^4$ and $R^5$. This is defined as 'preparation process 1' hereafter.

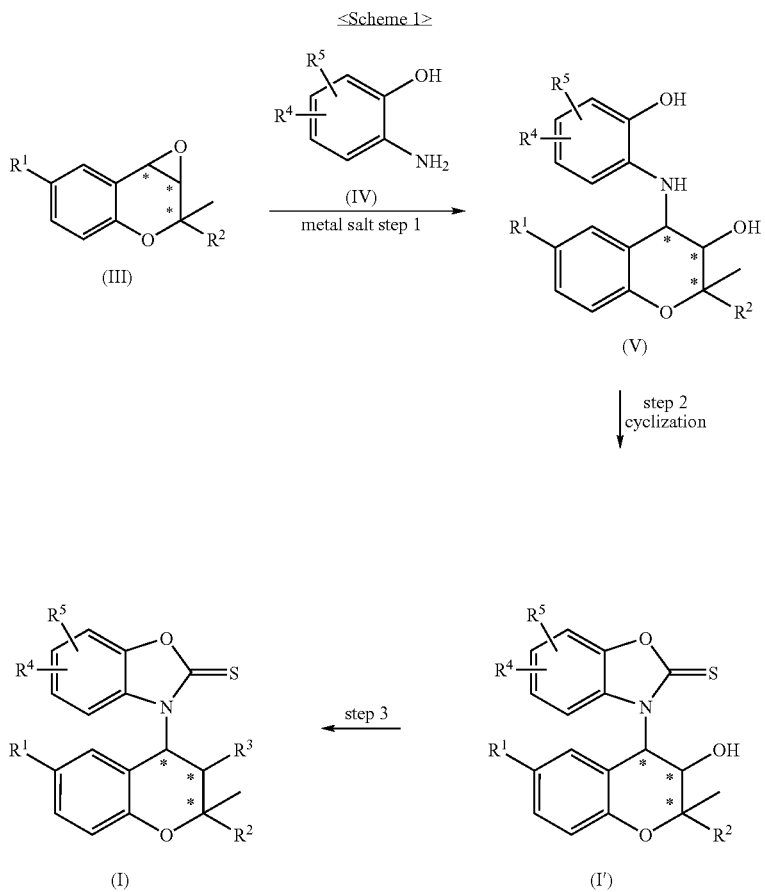

(Wherein, $R^1$, $R^2$, $R^3$, $R^4$, $R^5$ and * are as defined in <Formula 1>.)

The present invention also provides another process to prepare a compound of Formula (I). As shown in <Scheme 2>, cyclization of 2-aminophenol of formula (IV) using thiocarbonyl transfer reagent gives 2-thioxobenzoxazole of formula (VI). Then, epoxide ring opening of compound (III) is accomplished by reaction with a compound (VI) in the presence of a proper base, giving a compound of Formula (I'). Finally, a benzopyran derivative (I) can be prepared by changing substituents. This is defined as 'preparation process 2' hereafter.

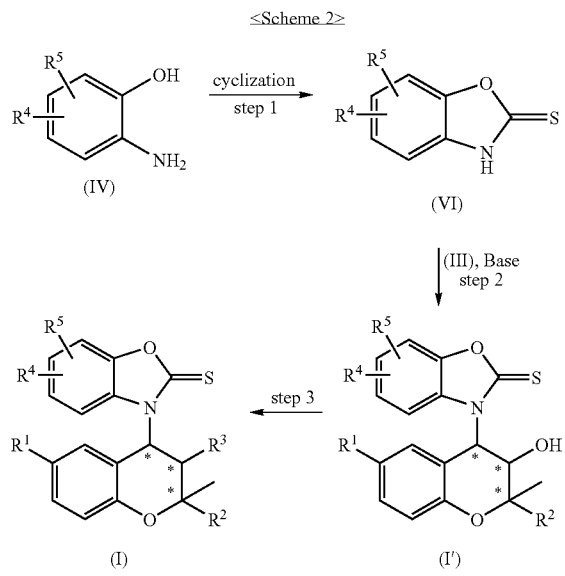

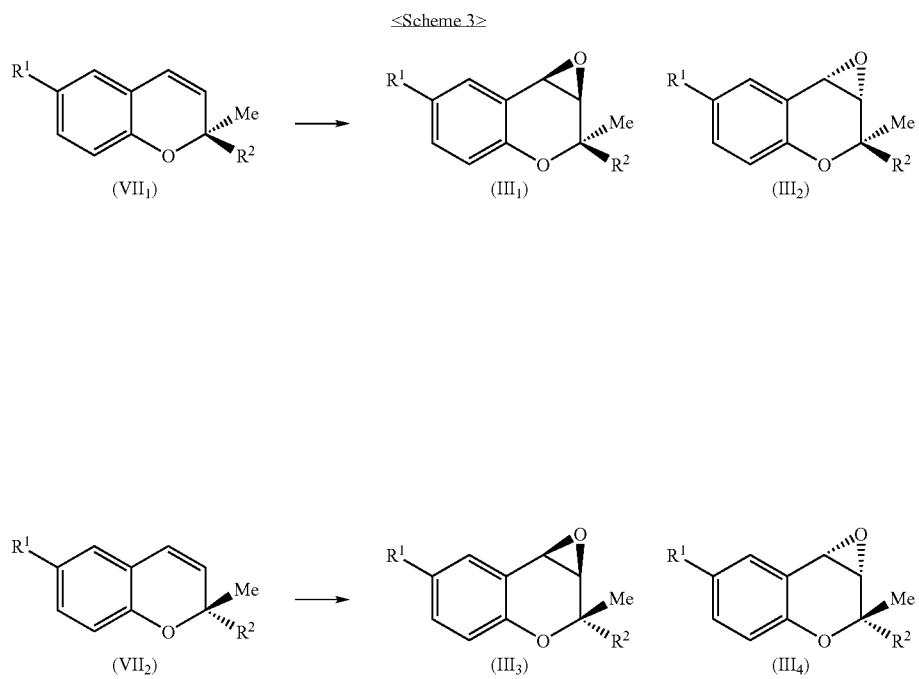

(Wherein, $R^1$, $R^2$, $R^3$, $R^4$, $R^5$ and * are as defined in <Formula 1>.)

In the present invention, a compound of <Formula 1> can be prepared in the form of an individual diastereomer from the corresponding diastereomer of starting material. Each diastereomer can also be obtained by separating the diastereomeric mixture of compound (I) prepared from a diastereomeric mixture of starting material. The separation of diastereomers can be performed by generally known column chromatography or recrystallization.

The preparation processes for benzopyran derivatives substituted with a thioxobenzoxazole derivative represented in <Formula 1> of the present invention are illustrated in more detail hereinafter.

I. Preparation of Starting Material (1) Preparation of Epoxide Compound (III)

Epoxide compound (III) used as a starting material in the above <Scheme 1> can be prepared by processes explained in Korean Patent No. 2000-60647 and U.S. Pat. No. 6,323,238.

As shown in the below <Scheme 3>, each diastereomer $(III_1)$, $(III_2)$, $(III_3)$ and $(III_4)$ of a compound (III) can be possibly prepared from olefin compounds $(VII_1)$ and $(VII_2)$ by employing an Mn (III) Salen epoxidation catalyst described in the above patents.

(Wherein, $R^1$ and $R^2$ are as defined in <Formula 1>.)

II. Preparation Process 1

The preparation process for the compounds of <Formula 1> represented in the above <Scheme 1> comprises the following steps:

1) preparing compound (V) by reaction of epoxide compound (III) and 2-aminophenol compound(IV) in the presence of a proper metal salt in proper solvent;

2) preparing 2-thioxobenzoxazole compound (I') by cyclization of the compound (V) using thiocarbonyl transfer reagent; and 3) preparing compound (I) by changing substituents of the compound (I').

The step 1) is a reaction of epoxide compound (III) with 2-aminophenol compound (IV) in proper solvent in the presence of a proper metal salt.

As a metal salt, $Mg(ClO_4)_2$, $CoCl_2$, $LiClO_4$, $NaClO_4$, $CaCl_2$, $ZnCl_2$, $LiBF_4$ or $Zn(Tf)_2$ can be used, and as a solvent, acetonitrile, tetrahydrofuran or dimethylformamide is available and acetonitrile is preferable among them. Reaction temperature ranges from room temperature to the boiling point of a solvent.

In case that an individual stereoisomer of epoxide compound (III) is used as a starting material, an individual stereoisomer with a stereochemistry corresponding to the compound used as a starting material will be obtained. As shown in the below <Scheme 4>, compounds ($V_1$), ($V_2$), ($V_3$) and ($V_4$) can be prepared from each epoxide compound ($III_1$), ($III_2$), ($III_3$) and ($III_4$).

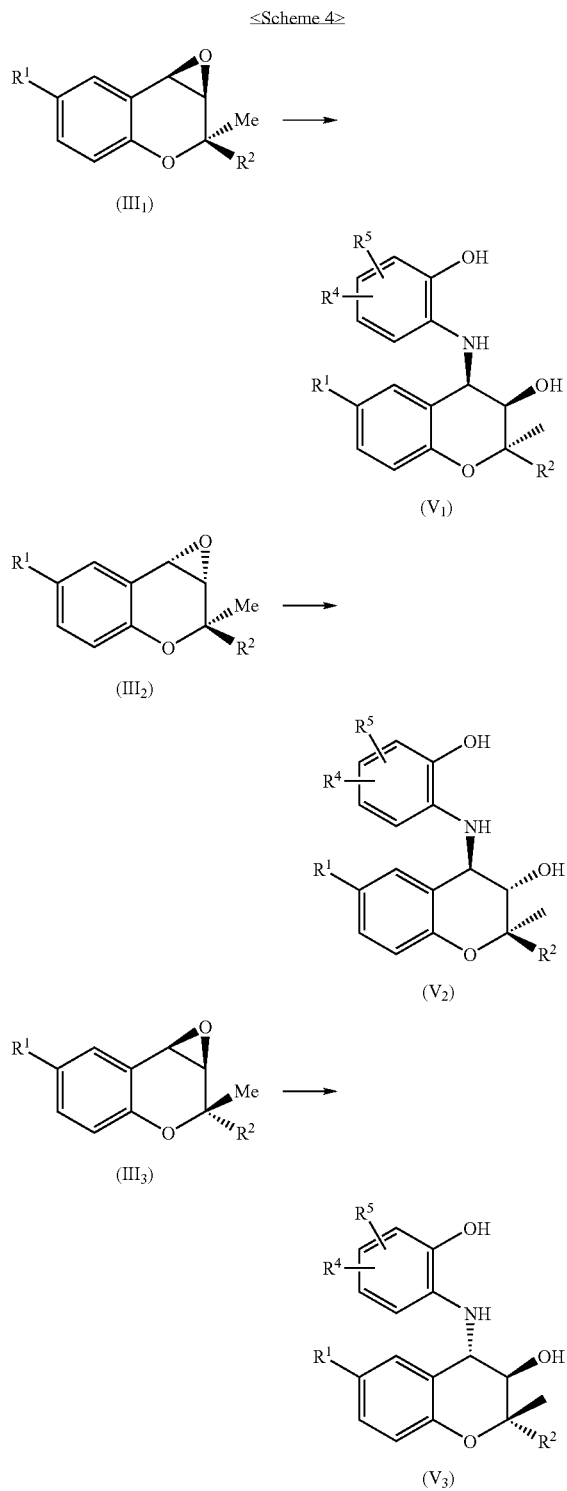

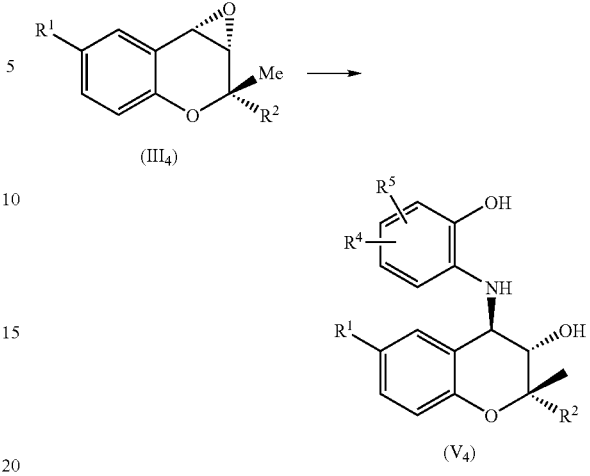

In cyclization of the above step 2), thiocarbonyl transfer reagent can be selected from a group consisting of carbon disulfide, and thiophosgens such as thiourea, 1,1'-thiocarbonyldiimidazole, 1,1'-thiocarbonyldi-1,2,4-triazole, di-2-pyridyl thiocarbonate, 1,1'-thiocarbonyl-2,2'-pyridone, etc.

In the above step 3), a compound (I) is prepared by changing substituents $R^1$, $R^2$, $R^3$, $R^4$ and $R^5$ by alkylation, acylation, reduction, or substitution, etc.

For example, as shown in <Scheme 5>, if $R^1$ of the compound (I) is amino group, the compound of the present invention can be prepared by reducing nitro group, for which hydrogenation is performed using a metal catalyst such as platinum, palladium on carbon (Pd/C) or Raney-nickel in proper solvent. An alternative way is reduction of nitro group using a reducing agent like $NaBH_4$ in the presence of $CuSO_4$, $Cu(OAc)_2$, $CoCl_2$, $SnCl_2$ or $NiCl_2$. In this reaction, preferable solvent is a mixture of water and methanol and reaction temperature rangs from room temperature to the boiling point of a solvent.

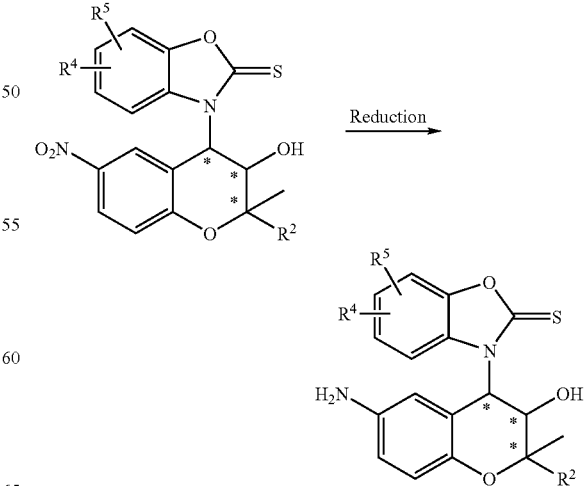

(Wherein, $R^2$, $R^4$, $R^5$ and * are as defined in <Formula 1>.)

III. Preparation Process 2

Another process to prepare a compound (I) of <Formula 1> is illustrated in step 1) of <Scheme 2>, a compound (VI) is prepared by cyclization of 2-aminophenol compound (I) such thiocarbonyl transfer reagents as in step 2) of the preparation process 1.

In step 2), a compound (I') is prepared by epoxide ring opening, in which a compound (VI) is reacted with epoxide compound (III) in the presence of base. Both inorganic base such as sodium hydride, potassium t-butoxide, sodium methoxide, etc and organic base such as 1,8-diazabicyclo[5.4.0]undec-7-ene (DBU), etc, are available.

In step 3), a compound (I) is prepared by changing substituents by the same process as used in the preparation process 1.

The present invention further provides a pharmaceutical composition for carioprotection containing benzopyran derivatives substituted with a thioxobenzoxazole derivative, represented in <Formula 1>, or pharmaceutically acceptable salts thereof as an effective ingredient.

When tested in ischemic heart models of Langendorff using isolated rat hearts, compounds of the present invention significantly prolong the time to contracture (TTC), an index of heart protection, and improve recovery of the cardiac function (left ventricular developed pressure×heart rate, LVDP× HR) after reperfusion, but reduce release of lactate dehydrogenase (LDH), an index for cell damage, which are similar or superior to cardioprotecting activity of BMS-180448, a control. In ischemic myocardium models using anesthetized rat, compounds of the present invention also show similar antiischemic activity to BMS-180448.

In conclusion, the compounds of the present invention show excellent cardioprotecting activity in vitro and in vivo as well, so that they can be effectively applied as a cardioprotective medicine and a preventing or therapeutic agent for both ischemic heart diseases such as myocardial infarction, unstable angina pectoris, etc, and other troubles, caused by thrombolytics or reperfusion therapy like PTCA (percutaneous transluminal coronary angioplasty) and CABG (coronary artery bypass graft), such as decrease of myocardial contractility, damage of myocardial cells, change of energy metabolism, decline of cognitive capability, etc.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

In the present invention, infrared spectroscopy, nuclear magnetic resonance spectroscopy, mass spectroscopy, liquid chromatography, x-ray crystallography, polarimetry were used along with the comparison of estimated results of elemental analysis of the representative compounds with analyzed results of them in order to confirm their molecular structures.

Example 1

Preparation of (2R,3R,4S)-6-nitro-3,4-dihydro-3-hydroxy-2-dimethoxymethyl-2-methyl-4-(2-thioxobenzoxazol-3-yl)-2H-1-benzopyran <Step 1> Preparation of (2R,3R,4S)-6-nitro-3,4-dihydro-3-hydroxy-2-dimethoxymethyl-2-methyl-4-[(2-hydroxyphenyl)amino]-2H-1-benzopyran 400 mg (1.42 mmol) of epoxide compound (2R,3R,4R)-6-nitro-3,4-dihydro-3,4-epoxy-2-dimethoxymethyl-2-methyl-2H-1-benzopyran and 155 mg (1.42 mmol) of 2-aminophenol were dissolved in 1 ml of acetonitrile ($CH_3CN$), then 318 mg (1.42 mmol) of magnesium perchlorate [$Mg(ClO_4)_2$] was added thereto. The reaction was stirred at room temperature for 1 hour, 10 ml of saturated $NaHCO_3$ solution was added, and aqueous layer was extracted with 30 ml of ethyl acetate. Organic layer was dried over anhydrous $MgSO_4$, concentrated under reduced pressure. The residue was purified by column chromatography (hexane:ethyl acetate=2:1), to give 518 mg (yield: 93%) of the target compound.

$^1$H NMR (200 MHz, $CDCl_3$) δ1.39(s, 3H), 3.61(s, 3H), 3.62(s, 3H), 3.85(s, 1H), 4.13(d, 1H), 4.23(d, 1H), 4.44(s, 1H), 6.75(br-s, 1H), 6.78-6.93(m, 5H), 8.06(dd, 1H), 8.45(d, 1H)

<Step 2> Preparation of (2R,3R,4S)-6-nitro-3,4-dihydro-3-hydroxy-2-dimethoxymethyl-2-methyl-4-(2-thioxobenzoxazol-3-yl)-2H-1-benzopyran 800 mg (2.05 mmol) of the compound obtained in the above step 1 was dissolved in 8 ml of $CH_2Cl_2$, then 470 mg (2.05 mmol) of di-2-pyridyl thionocarbonate and 25 mg (0.2 mmol) of 4-dimethylaminopyridine were added thereto. The reaction was stirred at room temperature for 2 hours, 20 ml of saturated $NaHCO_3$ solution was added, and aqueous layer was extracted with 30 ml of dichloromethane. Organic layer was washed with brine and dried over anhydrous $MgSO_4$, and concentrated under reduced pressure. The residue was purified by silica gel column chromatography (hexane:ethyl acetate=1:1), to give 220 mg (yield: 97%) of the target compound.

$^1$H NMR (200 MHz, $CDCl_3$) δ1.53(s, 3H), 3.62(s, 3H), 3.66(s, 3H), 4.50(s, 1H), 4.83(dd, 1H), 6.42(d, 1H), 6.51(d, 1H), 7.02-7.23(m, 2H), 7.38(d, 1H), 7.78(d, 1H), 8.15(dd, 1H)

Example 2

Preparation of (2R,3S,4R)-6-nitro-3,4-dihydro-3-hydroxy-2-dimethoxymethyl-2-methyl-4-(2-thioxobenzoxazol-3-yl)-2H-1-benzopyran <Step 1> Preparation of (2R,3S,4R)-6-nitro-3,4-dihydro-3-hydroxy-2-dimethoxymethyl-2-methyl-4-[(2-hydroxyphenyl)amino]-2H-1-benzopyran 500 mg (1.78 mmol) of epoxide compound (2R,3S,4S)-6-nitro-3,4-dihydro-3,4-epoxy-2-dimethoxymethyl-2-methyl-2H-1-benzopyran and 194 mg(1.78 mmol) of 2-aminophenol were reacted according to the procedure described in the above step 1 of the example 1, to give 615 mg (yield: 89%) of the target compound.

$^1$H NMR (200 MHz, $CDCl_3$) δ1.50(s, 3H), 3.52(s, 6H), 4.05-4.23(m, 3H), 4.47(s, 1H), 4.60(br-s, 1H), 6.71-6.96(m, 5H), 8.08(dd, 1H), 8.38(d, 1H)

\<Step 2\> Preparation of (2R,3S,4R)-6-nitro-3,4-dihydro-3-hydroxy-2-dimethoxymethyl-2-methyl-4-(2-thioxobenzoxazol-3-yl)-2H-1-benzopyran Reaction was performed with 280 mg (0.72 mmol) of the compound prepared in the above step 1 according to the procedure described in the step 2 of the example 1, to give 270 mg (yield: 86%) of the target compound.

$^1$H NMR (200 MHz, CDCl$_3$) δ1.67(s, 3H), 3.53(s, 3H), 3.57(s, 3H), 4.27(dd, 1H), 4.60(s, 1H), 6.32(d, 1H), 6.78(d, 1H), 7.00-7.28(m, 3H), 7.43(d, 1H), 7.76(d, 1H), 8.16(dd, 1H)

Example 3

Preparation of (2S,3R,4S)-6-nitro-3,4-dihydro-3-hydroxy-2-dimethoxymethyl-2-methyl-4-(2-thioxobenzoxazol-3-yl)-2H-1-benzopyran

\<Step 1\> Preparation of (2S,3R,4S)-6-nitro-3,4-dihydro-3-hydroxy-2-dimethoxymethyl-2-methyl-4-[(2-hydroxyphenyl)amino]-2H-1-benzopyran 300 mg (1.07 mmol) of epoxide compound (2S,3R,4R)-6-nitro-3,4-dihydro-3,4-epoxy-2-dimethoxymethyl-2-methyl-2H-1-benzopyran and 117 mg(1.07 mmol) of 2-aminophenol were reacted according to the procedure described in the above step 1 of the example 1, to give 329 mg (yield: 79%) of the target compound.

$^1$H NMR (200 MHz, CDCl$_3$) δ1.50(s, 3H), 3.52(s, 6H), 4.05-4.23(m, 3H), 4.47(s, 1H), 4.60(br-s, 1H), 6.71-6.96(m, 5H), 8.08(dd, 1H), 8.38(d, 1H)

\<Step 2\> Preparation of (2S,3R,4S)-6-nitro-3,4-dihydro-3-hydroxy-2-dimethoxymethyl-2-methyl-4-(2-thioxobenzoxazol-3-yl)-2H-1-benzopyran Reaction was performed with 250 mg (0.64 mmol) of the compound prepared in the above step 1 according to the procedure described in the step 2 of the example 1, to give 242 mg (yield: 88%) of the target compound.

$^1$H NMR (200 MHz, CDCl$_3$) δ1.67(s, 3H), 3.54(s, 3H), 3.57(s, 3H), 4.27(dd, 1H), 4.60(s, 1H), 6.33(d, 1H), 6.78(d, 1H), 7.00-7.22(m, 3H), 7.43(d,1 H), 7.76(d, 1H), 8.16(dd, 1H)

Example 4

Preparation of (2S,3S,4R)-6-nitro-3,4-dihydro-3-hydroxy-2-dimethoxymethyl-2-methyl-4-(2-thioxobenzoxazol-3-yl)-2H-1-benzopyran

\<Step 1\> Preparation of (2S,3S,4R)-6-nitro-3,4-dihydro-3-hydroxy-2-dimethoxymethyl-2-methyl-4-[(2-hydroxyphenyl)amino]-2H-1-benzopyran Reaction was performed with 1 g (3.56 mmol) of epoxide compound (2S,3S,4S)-6-nitro-3,4-dihydro-3,4-epoxy-2-dimethoxymethyl-2-methyl-2H-1-benzopyran and 389 mg (3.56 mmol) of 2-aminophenol according to the procedure described in the step 1 of the example 1, to give 1.24 g (yield: 89%) of the target compound.

$^1$H NMR (200 MHz, CDCl$_3$) δ1.39(s, 3H), 3.61(s, 3H), 3.62(s, 3H), 3.85(s, 1H), 4.13(d, 1H), 4.23(d, 1H), 4.44(s, 1H), 6.75(br-s, 1H), 6.78-6.93(m, 5H), 8.06(dd, 1H), 8.45(d, 1H)

\<Step 2\> Preparation of (2S,3S,4R)-6-nitro-3,4-dihydro-3-hydroxy-2-dimethoxymethyl-2-methyl-4-(2-thioxobenzoxazol-3-yl)-2H-1-benzopyran Reaction was performed with 350 mg (0.90 mmol) of the compound prepared in the above step 1 according to the procedure described in the step 2 of the example 1, to give 338 mg (yield: 87%) of the target compound.

$^1$H NMR (200 MHz, CDCl$_3$) δ1.53(s, 3H), 3.62(s, 3H), 3.66(s, 3H), 4.50(s, 1H), 4.83(dd, 1H), 6.42(d, 1H), 6.51(d, 1H), 7.02-7.23(m, 2H), 7.38(d, 1H), 7.78(d, 1H), 8.15(dd, 1H)

Example 5

Preparation of (2R,3R,4S)-6-nitro-3,4-dihydro-3-hydroxy-2-dimethoxymethyl-2-methyl-4-(6-methyl-2-thioxobenzoxazol-3-yl)-2H-1-benzopyran

\<Step 1\> Preparation of (2R,3R,4S)-6-nitro-3,4-dihydro-3-hydroxy-2-dimethoxymethyl-2-methyl-4-[(4-methyl-2-hydroxyphenyl)amino]-2H-1-benzopyran Reaction was performed with 300 mg(1.07 mmol) of epoxide compound (2R,3R,4R)-6-nitro-3,4-dihydro-3,4-epoxy-2-dimethoxymethyl-2-methyl-2H-1-benzopyran and 131 mg (1.07 mmol) of 5-methyl-2-aminophenol according to the procedure described in the step 1 of the example 1, to give 281 mg (yield: 65%) of the target compound.

$^1$H NMR (200 MHz, CDCl$_3$) δ1.36(s, 3H), 2.26(s, 3H), 3.61(s, 3H), 3.62(s, 3H), 3.91(s, 1H), 4.18(d, 1H), 4.26(brms, 1H), 4.41(s, 1H), 6.63-6.71(m, 3H), 6.86(dd, 2H), 806(dd, 1H), 8.54(d, 1H) Mass: 405(M+), 340, 272, 190, 144, 123, 75

\<Step 2\> Preparation of (2R,3R,4S)-6-nitro-3,4-dihydro-3-hydroxy-2-dimethoxymethyl-2-methyl-4-(6-methyl-2-thioxobenzoxazol-3-yl)-2H-1-benzopyran Reaction was performed with 300 mg (0.74 mmol) of the compound prepared in the above step 1 according to the procedure described in the step 2 of the example 1, to give 264 mg (yield: 80%) of the target compound.

$^1$H NMR (200 MHz, CDCl$_3$) δ1.52(s, 3H), 2.37(s, 3H), 3.53(d, 3H), 4.46(s, 1H), 4.80(dd, 1H), 6.27(d, 1H), 6.47(d, 1H), 6.85(d, 1H), 7.07(d, 1H). 7.22(s, 1H), 7.75(d, 1H), 8.13 (dd, 1H)

Example 6

Preparation of (2R,3R,4S)-6-nitro-3,4-dihydro-3-hydroxy-2-dimethoxymethyl-2-methyl-4-(4-methyl-2-thioxobenzoxazol-3-yl)-2H-1-benzopyran

\<Step 1\> Preparation of (2R,3R,4S)-6-nitro-3,4-dihydro-3-hydroxy-2-dimethoxymethyl-2-methyl-4-[(6-methyl-2-hydroxyphenol)amino]-2H-1-benzopyran Reaction was performed with 1 g (3.56 mmol) of epoxide compound (2R,3R,4R)-6-nitro-3,4-dihydro-3,4-epoxy-2-dimethoxymethyl-2-methyl-2H-1-benzopyran and 0.44 g (3.56 mmol) of 3-methyl-2-aminophenol according to the procedure described in the step 1 of the example 1, to give 1.15 g (yield: 80%) of the target compound.

¹H NMR (200 MHz, CDCl₃) δ1.32(s, 3H), 2.33(s, 3H), 3.23(s, 1H), 3.63(s, 3H), 3.65(s, 3H), 4.23(d, 1H), 4.26(d, 1H), 4.42(s, 1H), 4.48(d, 1H), 6.78-6.86(m, 3H), 6.89(d, 1H), 7.51(s, 1H), 8.01-8.07(dd, 1H), 8.37(d, 1H)

<Step 2> Preparation of (2R,3R,4S)-6-nitro-3,4-dihydro-3-hydroxy-2-dimethoxymethyl-2-methyl-4-(4-methyl-2-thioxobenzoxazol-3-yl)-2H-1-benzopyran Reaction was performed with 300 mg (0.74 mmol) of the compound prepared in the above step 1 according to the procedure described in the step 2 of the example 1, to give 137 mg (yield: 42%) of the target compound.
¹H NMR (200 MHz, CDCl₃) δ1.41(s, 3H), 2.73(s, 3H), 3.60(s, 3H), 3.68(s, 3H), 4.52(s, 1H), 5.58(d, 1H), 5.59(d, 1H), 7.02(d, 1H), 7.11-7.27(m, 3H), 7.76(d, 1H), 8.10(dd, 1H)

Example 7

Preparation of (2R,3R,4S)-6-nitro-3,4-dihydro-3-hydroxy-2-dimethoxymethyl-2-methyl-4-(5-chloro-2-thioxobenzoxazol-3-yl)-2H-1-benzopyran <Step 1> Preparation of (2R,3R,4S)-6-nitro-3,4-dihydro-3-hydroxy-2-dimethoxymethyl-2-methyl-4-[(5-chloro-2-hydroxyphenyl)amino]-2H-1-benzopyran Reaction was performed with 700 mg (2.48 mmol) of epoxide compound (2R,3R,4R)-6-nitro-3,4-dihydro-3,4-epoxy-2-dimethoxymethyl-2-methyl-2H-1-benzopyran and 356 mg (2.48 mmol) of 4-chloro-2-aminophenol according to the procedure described in the step 1 of the example 1, to give 791 mg (yield: 89%) of the target compound.
¹H NMR (200 MHz, CDCl₃) δ1.41(s, 3H), 3.61(s, 3H), 3.62(s, 3H), 3.77(s, 1H), 4.22(d, 1H), 4.43(m, 2H), 6.67(d, 2H), 6.80(d, 1H), 6.91(d, 1H), 8.07(dd, 1H), 8.35(d, 1H)

<Step 2> Preparation of (2R,3R,4S)-6-nitro-3,4-dihydro-3-hydroxy-2-dimethoxymethyl-2-methyl-4-(5-chloro-2-thioxobenzoxazol-3-yl)-2H-1-benzopyran Reaction was performed with 350 mg (0.82 mmol) of the compound prepared in the above step 1 according to the procedure described in the step 2 of the example 1, to give 348 mg (yield: 91%) of the target compound.
¹H NMR (200 MHz, CDCl₃) δ1.52(s, 3H), 3.52(d, 1H), 3.64(s, 3H), 3.67(s, 3H), 4.52(s, 1H), 4.78(dd, 1H), 6.41(d, 1H), 6.47(d, 1H), 7.11(d, 1H), 7.20(dd, 1H), 7.34(d, 1H), 7.77(d, 1H), 8.18(dd, 1H)

Example 8

Preparation of (2R,3R,4S)-6-nitro-3,4-dihydro-3-hydroxy-2-dimethoxymethyl-2-methyl-4-(5-methyl-2-thioxobenzoxazol-3-yl)-2H-1-benzopyran <Step 1> Preparation of (2R,3R,4S)-6-nitro-3,4-dihydro-3-hydroxy-2-dimethoxymethyl-2-methyl-4-[(5-methyl-2-hydroxyphenyl)amino]-2H-1-benzopyran Reaction was performed with 1 g (3.56 mmol) of epoxide compound (2R,3R,4R)-6-nitro-3,4-dihydro-3,4-epoxy-2-dimethoxymethyl-2-methyl-2H-1-benzopyran and 0.44 g (3.56 mmol) of 5-methyl-2-aminophenol according to the procedure described in the step 1 of the example 1, to give 1.32 g (yield: 92%) of the target compound.
¹H NMR (200 MHz, CDCl₃) δ1.39(s, 3H), 2.24(s, 3H), 3.31(s, 3H), 3.61(s, 3H), 3.77(d, 1H), 4.21(d, 1H), 4.43(s, 1H), 6.20(s, 1H), 6.59(d, 1H), 6.70(d, 1H), 6.92(d, 1H), 8.03(dd, 1H), 8.44(d, 1H)

<Step 2> Preparation of (2R,3R,4S)-6-nitro-3,4-dihydro-3-hydroxy-2-dimethoxymethyl-2-methyl-4-(5-methyl-2-thioxobenzoxazol-3-yl)-2H-1-benzopyran Reaction was performed with 300 mg (0.74 mmol) of the compound prepared in the above step 1 according to the procedure described in the step 2 of the example 1, to give 291 mg (yield: 88%) of the target compound.
¹H NMR (200 MHz, CDCl₃) δ1.66(s, 3H), 2.25(s, 3H), 3.36(s, 3H), 3.67(s, 3H), 4.53(s, 1H), 4.86(d, 1H), 6.21(s, 1H), 6.53(d, 1H), 7.09(d, 1H), 7.13(d, 1H), 7.27(d, 1H), 7.76(s, 1H), 8.13(dd, 1H)

Example 9

Preparation of (2R,3R,4S)-6-nitro-3,4-dihydro-3-hydroxy-2-dimethoxymethyl-2-methyl-4-(6-nitro-2-thioxobenzoxazol-3-yl)-2H-1-benzopyran <Step 1> Preparation of (2R,3R,4S)-6-nitro-3,4-dihydro-3-hydroxy-2-dimethoxymethyl-2-methyl-4-[(4-nitro-2-hydroxyphenyl)amino]-2H-1-benzopyran Reaction was performed with 1 g (3.56 mmol) of epoxide compound (2R,3R,4R)-6-nitro-3,4-dihydro-3,4-epoxy-2-dimethoxymethyl-2-methyl-2H-1-benzopyran and 548 mg (3.56 mmol) of 5-nitro-2-aminophenol according to the procedure described in the step 1 of the example 1, to give 927 mg (yield: 60%) of the target compound.
¹H NMR (200 MHz, CDCl₃) δ1.50(s, 3H), 3.66(s, 6H), 4.40(d, 1H), 4.49(s, 1H), 4.75(t, 1H), 5.22(d, 1H), 6.61(d, 1H), 6.95(d, 1H), 7.46(d, 1H), 7.69(dd, 1H), 8.09(dd, 1H), 8.18(d, 1H)

<Step 2> Preparation of (2R,3R,4S)-6-nitro-3,4-dihydro-3-hydroxy-2-dimethoxymethyl-2-methyl-4-(6-nitro-2-thioxobenzoxazol-3-yl)-2H-1-benzopyran Reaction was performed with 250 mg (0.57 mmol) of the compound prepared in the above step 1 according to the procedure described in the step 2 of the example 1, to give 140 mg (yield: 51%) of the target compound.
¹H NMR (200 MHz, CDCl₃) δ1.54(s, 3H), 3.54(s, 1H), 3.63(s, 3H), 3.68(s, 3H), 4.51(s, 1H), 4.80(d, 1H), 6.47(d, 1H), 6.52(d, 1H), 7.12(d, 1H), 7.76(dd, 1H), 8.06(dd, 1H), 8.17(dd, 1H), 8.25(d, 1H)

Example 10

Preparation of (2R,3R,4S)-6-nitro-3,4-dihydro-3-hydroxy-2-dimethoxymethyl-2-methyl-4-(5-methoxy-2-thioxobenzoxazol-3-yl)-2H-1-benzopyran <Step 1> Preparation of (2R,3R,4S)-6-nitro-3,4-dihydro-3-hydroxy-2-dimethoxymethyl-2-methyl-4-[(5-methoxy-2-hydroxyphenyl)amino]-2H-1-benzopyran Reaction was performed with 200 mg (0.71 mmol) of epoxide compound (2R,3R,4R)-6-nitro-3,4-dihydro-3,4-epoxy-2-dimethoxymethyl-2-methyl-2H-1-benzopyran and 99 mg (0.71 mmol) of 4-methoxy-2-aminophenol according to the procedure described in the step 1 of the example 1, to give 225 mg (yield: 89%) of the target compound.

$^1$H NMR (200 MHz, CDCl$_3$) δ1.38(s, 3H), 3.60(s, 3H), 3.61(s, 3H), 3.60-3.80(br-s, 4H), 4.20(br-s, 2H), 4.43(s, 1H), 6.20-6.80(br-s, 3H), 6.90(d, 1H), 8.05(dd, 1H), 8.41(d, 1H)

<Step 2> Preparation of (2R,3R,4S)-6-nitro-3,4-dihydro-3-hydroxy-2-dimethoxymethyl-2-methyl-4-(5-methoxy-2-thioxobenzoxazol-3-yl)-2H-1-benzopyran Reaction was performed with 320 mg (0.76 mmol) of the compound prepared in the above step 1 according to the procedure described in the step 2 of the example 1, to give 336 mg (yield: 96%) of the target compound.

$^1$H NMR (200 MHz, CDCl$_3$) δ1.52(s, 3H), 3.46(s, 1H), 3.61-3.66(m, 6H), 4.49(s, 1H), 4.82(dd, 1H), 5.96(d, 1H), 6.48(d, 1H), 6.73(dd, 1H), 7.07(d, 1H), 7.30(d, 1H), 7.78(d, 1H), 8.14(dd, 1H)

Example 11

Preparation of (2R,3R,4S)-6-nitro-3,4-dihydro-3-hydroxy-2-dimethoxymethyl-2-methyl-4-(5-bromo-2-thioxobenzoxazol-3-yl)-2H-1-benzopyran <Step 1> Preparation of (2R,3R,4S)-6-nitro-3,4-dihydro-3-hydroxy-2-dimethoxymethyl-2-methyl-4-[(5-bromo-2-hydroxyphenyl)amino]-2H-1-benzopyran Reaction was performed with 500 mg (1.78 mmol) of epoxide compound (2R,3R,4R)-6-nitro-3,4-dihydro-3,4-epoxy-2-dimethoxymethyl-2-methyl-2H-1-benzopyran and 334 mg (1.78 mmol) of 4-bromo-2-aminophenol according to the procedure described in the step 1 of the example 1, to give 535 mg (yield: 64%) of the target compound.

$^1$H NMR (200 MHz, CDCl$_3$) δ1.41(s, 3H), 3.62(s, 3H), 3.76(s, 1H), 4.24(d, 1H), 4.43(m, 2H), 6.67(d, 1H), 6.79(dd, 1H), 6.89(d, 1H), 6.93(d, 1H), 8.05(dd, 1H), 8.35(d, 1H)

<Step 2> Preparation of (2R,3R,4S)-6-nitro-3,4-dihydro-3-hydroxy-2-dimethoxymethyl-2-methyl-4-(5-bromo-2-thioxobenzoxazol-3-yl)-2H-1-benzopyran Reaction was performed with 300 mg (0.64 mmol) of the compound prepared in the above step 1 according to the procedure described in the step 2 of the example 1, to give 316 mg (yield: 97%) of the target compound.

$^1$H NMR (200 MHz, CDCl$_3$) δ1.52(s, 3H), 3.64(s, 3H), 3.67(s, 3H), 4.52(s, 1H), 4.82(d, 1H), 6.44(d, 1H), 6.55(d, 1H), 7.13(d, 1H), 7.30(d, 1H), 7.34(dd, 1H), 7.77(d, 1H), 8.19(dd, 1H)

Example 12

Preparation of (2R,3R,4S)-6-nitro-3,4-dihydro-3-hydroxy-2-dimethoxymethyl-2-methyl-4-(5-t-butoxy-2-thioxobenzoxazol-3-yl)-2H-1-benzopyran <Step 1> Preparation of (2R,3R,4S)-6-nitro-3,4-dihydro-3-hydroxy-2-dimethoxymethyl-2-methyl-4-(5-t-butoxy-2-hydroxyphenyl)amino]-2H-1-benzopyran Reaction was performed with 500 mg (1.78 mmol) of epoxide compound (2R,3R,4R)-6-nitro-3,4-dihydro-3,4-epoxy-2-dimethoxymethyl-2-methyl-2H-1-benzopyran and 294 mg (1.78 mmol) of 4-t-butoxy-2-aminophenol according to the procedure described in the step 1 of the example 1, to give 600 mg (yield: 76%) of the target compound.

$^1$H NMR (200 MHz, CDCl$_3$) δ1.27(s, 9H), 1.35(s, 3H), 3.62(s, 3H), 3.63(s, 3H), 3.82(br-s, 1H), 3.94(s, 1H), 4.29(d, 1H), 4.42(s, 1H), 6.77-6.95(m, 5H), 8.06(dd, 1H), 8.58(d, 1H)

<Step 2> Preparation of (2R,3R,4S)-6-nitro-3,4-dihydro-3-hydroxy-2-dimethoxymethyl-2-methyl-4-(5-t-butoxy-2-thioxobenzoxazol-3-yl)-2H-1-benzopyran Reaction was performed with 350 mg (0.78 mmol) of the compound prepared in the above step 1 according to the procedure described in the step 2 of the example 1, to give 349 mg (yield: 92%) of the target compound.

$^1$H NMR (200 MHz, CDCl$_3$) δ1.11(s, 9H), 1.52(s, 3H), 3.37(d, 1H), 3.58(s, 3H), 3.67(s, 3H), 4.50(s, 1H), 4.92(dd, 1H), 6.36(d, 1H), 6.45(d, 1H), 7.11(d, 1H), 7.24-7.32(m, 2H), 7.81(d, 1H), 8.14(dd, 1H)

Example 13

Preparation of (2R,3R,4S)-6-nitro-3,4-dihydro-3-hydroxy-2-dimethoxymethyl-2-methyl-4-(6-fluoro-2-thioxobenzoxazol-3-yl)-2H-1-benzopyran <Step 1> Preparation of (2R,3R,4S)-6-nitro-3,4-dihydro-3-hydroxy-2-dimethoxymethyl-2-methyl-4-[(5-fluoro-2-hydroxyphenyl)amino]-2H-1-benzopyran Reaction was performed with 500 mg (1.78 mmol) of epoxide compound (2R,3R,4R)-6-nitro-3,4-dihydro-3,4-epoxy-2-dimethoxymethyl-2-methyl-2H-1-benzopyran and 226 mg (1.78 mmol) of 5-fluoro-2-aminophenol according to the procedure described in the step 1 of the example 1, to give 365 mg (yield: 50%) of the target compound.

1H NMR (200 MHz, CDCl3) δ1.35(s, 3H), 3.54(s, 1H), 3.63(s, 3H), 3.64(s, 3H), 4.19(m, 3H), 4.42(s, 1H), 6.57(ddd, 1H), 6.65(dd, 1H), 6.90(d, 1H), 6.93(dd, 1H), 7.72(br-s, 1H), 8.07(dd, 1H), 8.56(d, 1H)

<Step 2> Preparation of (2R,3R,4S)-6-nitro-3,4-dihydro-3-hydroxy-2-dimethoxymethyl-2-methyl-4-(6-fluoro-2-thioxobenzoxazol-3-yl)-2H-1-benzopyran Reaction was performed with 309 mg (0.76 mmol) of the compound prepared in the above step 1 according to the procedure described in the step 2 of the example 1, to give 290 mg (yield: 85%) of the target compound.

$^1$H NMR (200 MHz, CDCl$_3$) δ1.56(s, 3H), 3.62(s, 3H), 3.66(s, 3H), 4.50(s, 1H), 4.82(d, 1H), 6.35(dd, 1H), 6.49(d, 1H), 6.83(ddd, 1H), 7.11(d, 1H), 7.20(dd, 1H), 7.78(d, 1H), 8.17(dd, 1H)

Example 14

Preparation of (2R,3R,4S)-6-nitro-3,4-dihydro-3-hydroxy-2-dimethoxymethyl-2-methyl-4-(4-methoxycarbonyl-2-thioxobenzoxazol-3-yl)-2H-1-benzopyran <Step 1> Preparation of (2R,3R,4S)-6-nitro-3,4-dihydro-3-hydroxy-2-dimethoxymethyl-2-methyl-4-(6-methoxycarbonyl-2-hydroxyphenyl)amino]-2H-1-benzopyran Reaction was performed with 163 mg (0.58 mmol) of epoxide compound (2R,3R,4R)-6-nitro-3,4-dihydro-3,4-epoxy-2-dimethoxymethyl-2-methyl-2H-1-benzopyran and 97 mg (0.58 mmol) of 2-amino-hydroxybenzoic acid methyl ester according to the procedure described in the step 1 of the example 1, to give 214 mg (yield: 83%) of the target compound.

$^1$H NMR (200 MHz, CDCl$_3$) δ1.35(s, 3H), 3.64(s, 3H), 3.65(s, 3H), 3.86(s, 3H), 4.30(d, 1H), 4.43(s, 1H), 4.67(t, 1H), 6.87(t, 1H), 7.08(d, 1H), 7.17(d, 1H), 7.61(dd, 1H), 8.05(dd, 1H), 8.08(d, 1H), 8.21(d, 1H)

<Step 2> Preparation of (2R,3R,4S)-6-nitro-3,4-dihydro-3-hydroxy-2-dimethoxymethyl-2-methyl-4-(4-methoxycarbonyl-2-thioxobenzoxazol-3-yl)-2H-1-benzopyran Reaction was performed with 204 mg (0.46 mmol) of the compound prepared in the above step 1 according to the procedure described in the step 2 of the example 1, to give 152 mg (yield: 68%) of the target compound.

$^1$H NMR (200 MHz, CDCl$_3$) δ1.36(s, 3H), 3.57(s, 3H), 3.67(s, 3H), 3.94(s, 3H), 4.46(s, 1H), 5.41(d, 1H), 6.70(d, 1H), 7.01(d, 1H), 7.34(ddd, 1H), 7.54(dd, 1H), 7.81(dd, 1H), 8.01(d, 1H), 8.13(dd, 1H)

Example 15

Preparation of (2R,3R,4S)-6-nitro-3,4-dihydro-3-hydroxy-2-dimethoxymethyl-2-methyl-4-(5-methoxycarbonyl-2-thioxobenzoxazol-3-yl)-2H-1-benzopyran <Step 1> Preparation of (2R,3R,4S)-6-nitro-3,4-dihydro-3-hydroxy-2-dimethoxymethyl-2-methyl-4-[(5-methoxycarbonyl-2-hydroxyphenyl)amino]-2H-1-benzopyran Reaction was performed with 1.173 g (4.17 mmol) of epoxide compound (2R,3R,4R)-6-nitro-3,4-dihydro-3,4-epoxy-2-dimethoxymethyl-2-methyl-2H-1-benzopyran and 697 mg (4.17 mmol) of 3-amino-4-hydroxybenzoic acid methyl ester according to the procedure described in the step 1 of the example 1, to give 305 mg (yield: 16%) of the target compound.

$^1$H NMR (200 MHz, CDCl$_3$) δ1.42(s, 3H), 3.62(s, 6H), 3.85(s, 3H), 4.27(d, 1H), 4.44(m, 2H), 6.80(d, 1H), 6.93(d, 1H), 7.42(dd, 1H), 7.53(d, 1H), 8.04(dd, 1H), 8.34(d, 1H)

<Step 2> Preparation of (2R,3R,4S)-6-nitro-3,4-dihydro-3-hydroxy-2-dimethoxymethyl-2-methyl-4-(5-methoxycarbonyl-2-thioxobenzoxazol-3-yl)-2H-1-benzopyran Reaction was performed with 290 mg (0.65 mmol) of the compound prepared in the above step 1 according to the procedure described in the step 2 of the example 1, to give 152 mg (yield: 68%) of the target compound.

$^1$H NMR (200 MHz, CDCl$_3$) δ1.54(s, 3H), 3.64(s, 3H), 3.68(s, 3H), 3.86(s, 3H), 4.53(s, 1H), 4.89(d, 1H), 6.52(d, 1H), 7.14(m, 2H), 7.47(d, 1H), 7.78(m, 1H), 7.95(dd, 1H), 8.15(m, 1H)

Example 16

Preparation of (2R,3R,4S)-6-nitro-3,4-dihydro-3-hydroxy-2-dimethoxymethyl-2-methyl-4-(5-trifluoromethyl-2-thioxobenzoxazol-3-yl)-2H-1-benzopyran <Step 1> Preparation of (2R,3R,4S)-6-nitro-3,4-dihydro-3-hydroxy-2-dimethoxymethyl-2-methyl-4-[(5-trifluoromethyl-2-hydroxyphenyl)amino]-2H-1-benzopyran Reaction was performed with 500 mg (1.78 mmol) of epoxide compound (2R,3R,4R)-6-nitro-3,4-dihydro-3,4-epoxy-2-dimethoxymethyl-2-methyl-2H-1-benzopyran and 315 mg (1.78 mmol) of 4-trifluoromethyl-2-aminophenol according to the procedure described in the step 1 of the example 1, to give 259 mg (yield: 32%) of the target compound.

$^1$H NMR (200 MHz, CDCl$_3$) δ1.42(s, 3H), 3.62(s, 3H), 3.62(s, 3H), 3.96(s, 1H), 4.28(d, 1H), 4.44(s, 1H), 4.45(d, 1H), 6.74(d, 1H), 6.89-7.00(m, 3H), 8.07(dd, 1H), 8.34(d, 1H)

<Step 2> Preparation of (2R,3R,4S)-6-nitro-3,4-dihydro-3-hydroxy-2-dimethoxymethyl-2-methyl-4-(5-trifluoromethyl-2-thioxobenzoxazol-3-yl)-2H-1-benzopyran Reaction was performed with 235 mg (0.51 mmol) of the compound prepared in the above step 1 according to the procedure described in the step 2 of the example 1, to give 195 mg (yield: 76%) of the target compound.

$^1$H NMR (200 MHz, CDCl$_3$) δ1.45(s, 0.6H), 1.53(s, 2.4H), 3.55(s, 1H), 3.61(s, 0.6H), 3.62(s, 2.4H), 3.67(s, 2.4H), 3.68 (s, 0.6H), 4.51(s, 1H), 4.85(d, 1H), 6.48(d, 1H), 6.63(s, 1H), 7.03(d, 0.2H), 7.12(d, 0.8H), 7.52-7.59(m, 2H), 7.73(d, 0.2H), 7.80(d, 0.8H), 8.18(dd, 1H)

Example 17

Preparation of (2R,3R,4S)-6-amino-3,4-dihydro-3-hydroxy-2-dimethoxymethyl-2-methyl-4-(2-thioxobenzoxazol-3-yl)-2H-1-benzopyran 200 mg (0.46 mmol) of the compound obtained in Example 1 was dissolved in 10 ml of methanol, to which 100 mg of Raney-Ni was added. Reaction was continued for 14 hours at room temperature with 3 atmospheric pressure of hydrogen gas. The reaction solution was filtered to eliminate Ni, and concentrated under reduced pressure. The residue was purified by silica gel column chromatography (hexane:ethyl acetate=2:1), to give 177 mg (yield: 96%) of the target compound.

$^1$H NMR (200 MHz, CDCl$_3$) δ1.43(s, 3H), 3.34(br-s, 2H), 3.47(br-s, 1H), 3.60(s, 3H), 3.62(s, 3H), 4.42(s, 1H), 4.75(d, 1H), 6.20(d, 1H), 6.31(d, 1H), 6.55-6.63(m, 2H), 6.78(d, 1H), 7.02-7.22(m, 2H), 7.35(dd, 1H)

Example 18

Preparation of (2S,3S,4R)-6-amino-3,4-dihydro-3-hydroxy-2-dimethoxymethyl-2-methyl-4-(2-thioxobenzoxazol-3-yl)-2H-1-benzopyran Reaction was performed with 214 mg (0.49 mmol) of the compound prepared in Example 4 according to the procedure described in the example 17, to give 174 mg (yield: 88%) of the target compound.
$^1$H NMR (200 MHz, CDCl$_3$) δ1.43(s, 3H), 3.34(br-s, 2H), 3.47(br-s, 1H), 3.60(s, 3H), 3.62(s, 3H), 4.42(s, 1H), 4.75(d, 1H), 6.21(d, 1H), 6.31(d, 1H), 6.57-6.63(m, 2H), 6.78(d, 1H), 7.06-7.26(m, 2H), 7.37(dd, 1H)

Example 19

Preparation of (2S,3R,4S)-6-amino-3,4-dihydro-3-hydroxy-2-dimethoxymethyl-2-methyl-4-(2-thioxobenzoxazol-3-yl)-2H-1-benzopyran Reaction was performed with 242 mg (0.56 mmol) of the compound prepared in Example 3 according to the procedure described in the example 17, to give 177 mg (yield: 79%) of the target compound.
$^1$H NMR (200 MHz, CDCl$_3$) δ1.56(s, 3H), 3.37(br-s, 2H), 3.43(br-s, 1H), 3.54(s, 3H), 3.60(s, 3H), 4.25(dd, 1H), 4.65(s, 1H), 6.19(d, 1H), 6.44(d, 1H), 6.54(d, 1H), 6.61(dd, 1H), 6.80(d, 1H), 7.09-7.23(m, 2H), 7.38(d, 1H)

Example 20

Preparation of (2R,3S,4R)-6-amino-3,4-dihydro-3-hydroxy-2-dimethoxymethyl-2-methyl-4-(2-thioxobenzoxazol-3-yl)-2H-1-benzopyran Reaction was performed with 187 mg (0.43 mmol) of the compound prepared in Example 2 according to the procedure described in the example 17, to give 142 mg (yield: 82%) of the target compound.
$^1$H NMR (200 MHz, CDCl$_3$) δ1.56(s, 3H), 3.36(br-s, 2H), 3.42(br-s, 1H), 3.54(s, 3H), 3.59(s, 3H), 4.24(dd, 1H), 4.65(s, 1H), 6.18(d, 1H), 6.44(d, 1H), 6.52(d, 1H), 6.61(dd, 1H), 6.79(d, 1H), 7.05-7.26(m, 2H), 7.36(d, 1H)

Example 21

Preparation of (2R,3R,4S)-6-amino-3,4-dihydro-3-hydroxy-2-dimethoxymethyl-2-methyl-4-(6-methyl-2-thioxobenzoxazol-3-yl)-2H-1-benzopyran Reaction was performed with 170 mg (0.38 mmol) of the compound prepared in Example 5 according to the procedure described in the example 17, to give 148 mg (yield: 93%) of the target compound.
$^1$H NMR (200 MHz, CDCl$_3$) δ1.42(s, 3H), 2.37(s, 3H), 3.32(s, 2H, NH2), 3.44(s, 1H, OH), 3.60(s, 3H), 3.61(s, 3H), 4.41(s, 1H), 4.73(d, 1H), 6.20(d, 1H), 6.28(d, 1H), 6.47(d, 1H), 6.58(dd, 1H), 6.78(d, 1H), 6.87(d, 1H), 7.18(s, 1H)

Example 22

Preparation of (2R,3R,4S)-6-amino-3,4-dihydro-3-hydroxy-2-dimethoxymethyl-2-methyl-4-(5-methyl-2-thioxobenzoxazol-3-yl)-2H-1-benzopyran Reaction was performed with 224 mg (0.50 mmol) of the compound prepared in Example 8 according to the procedure described in the example 17, to give 152 mg (yield: 73%) of the target compound.
$^1$H NMR (200 MHz, CDCl$_3$) δ1.42(s, 3H), 2.25(s, 3H), 3.61(s, 3H), 3.62(s, 3H), 4.44(s, 1H), 4.78(d, 1H), 6.20(s, 1H), 6.27(d, 1H), 6.39(s, 1H), 6.62(dd, 1H), 6.77(d, 1H), 6.95(d, 1H), 7.19(d, 1H)

Example 23

Preparation of (2R,3R,4S)-6-amino-3,4-dihydro-3-hydroxy-2-dimethoxymethyl-2-methyl-4-(4-methyl-2-thioxobenzoxazol-3-yl)-2H-1-benzopyran Reaction was performed with 107 mg (0.24 mmol) of the compound prepared in Example 6 according to the procedure described in the example 17, to give 82 mg (yield: 82%) of the target compound.
$^1$H NMR (200 MHz, CDCl$_3$) δ1.47(s, 3H), 1.91(s, 3H), 3.56(s, 3H), 3.36(s, 3H), 4.40(s, 1H), 4.79(d, 1H), 6.26(s, 1H), 6.59(dd, 1H), 6.71(s, 1H), 6.76(s, 1H), 6.95(d, 1H), 7.12(t, 1H), 7.23(d,1H)

Example 24

Preparation of (2R,3R,4S)-6-amino-3,4-dihydro-3-hydroxy-2-dimethoxymethyl-2-methyl-4-(5-chloro-2-thioxobenzoxazol-3-yl)-2H-1-benzopyran Reaction was performed with 218 mg (0.47 mmol) of the compound prepared in Example 7 according to the procedure described in the example 17, to give 167 mg (yield: 81%) of the target compound.
$^1$H NMR (200 MHz, CDCl$_3$) δ1.41(s, 3H), 3.37(br-s, 2H), 3.53(s, 1H), 3.62(s, 3H), 3.64(s, 3H), 4.43(s, 1H), 4.70(d, 1H), 6.19(d, 1H), 6.27(d, 1H), 6.58(d, 1H), 6.62(d, 1H), 6.79(d, 1H), 7.15(dd, 1H), 7.27(d, 1H)

Example 25

Preparation of (2R,3R,4S)-6-amino-3,4-dihydro-3-hydroxy-2-dimethoxymethyl-2-methyl-4-(5-methoxy-2-thioxobenzoxazol-3-yl)-2H-1-benzopyran Reaction was performed with 207 mg (0.45 mmol) of the compound prepared in Example 10 according to the procedure described in the example 17, to give 160 mg (yield: 82%) of the target compound.
$^1$H NMR (200 MHz, CDCl$_3$) δ1.41(s, 3H), 3.36(s, 1H), 3.47(br-s, 2H), 3.60(s, 3H), 3.62(s, 3H), 3.65(s, 3H), 4.41(s, 1H), 4.75(d, 1H), 6.14(d, 1H), 6.22(d, 1H), 6.28(d, 1H), 6.57(dd, 1H), 6.70(dd, 1H), 6.77(d, 1H), 7.24(d, 1H)

Example 26

Preparation of (2R,3R,4S)-6-amino-3,4-dihydro-3-hydroxy-2-dimethoxymethyl-2-methyl-4-(5-t-butoxy-2-thioxobenzoxazol-3-yl)-2H-1-benzopyran Reaction was performed with 220 mg (0.45 mmol) of the compound prepared in Example 12 according to the procedure described in the example 17, to give 167 mg (yield: 81%) of the target compound.
$^1$H NMR (200 MHz, CDCl$_3$) δ1.16(s, 3H), 1.42(s, 3H), 3.35(br-s, 3H), 3.56(s, 3H), 3.65(s, 3H), 4.40(s, 1H), 4.92(d, 1H), 6.24(s, 1H), 6.26(d, 1H), 6.59(m, 2H), 6.79(d, 1H), 7.20-7.23(m, 2H)

Example 27

Preparation of (2R,3R,4S)-6-amino-3,4-dihydro-3-hydroxy-2-dimethoxymethyl-2-methyl-4-(6-fluoro-2-thioxobenzoxazol-3-yl)-2H-1-benzopyran Reaction was performed with 231 mg (0.51 mmol) of the compound prepared in Example 13 according to the procedure described in the example 17, to give 43 mg (yield: 20%) of the target compound.
$^1$H NMR (200 MHz, CDCl$_3$) δ1.42(s, 3H), 3.60(s, 3H), 3.62(s, 3H), 4.41(s, 1H), 4.73(d, 1H), 6.20(d, 1H), 6.28(d, 1H), 6.52(dd, 1H), 6.60(ddd, 1H), 6.76(d, 1H), 6.81(dd, 1H), 7.13(dd, 1H)

Example 28

Preparation of (2R,3R,4S)-6-amino-3,4-dihydro-3-hydroxy-2-dimethoxymethyl-2-methyl-4-(5-methoxycarbonyl-2-thioxobenzoxazol-3-yl)-2H-1-benzopyran Reaction was performed with 155 mg (0.32 mmol) of the compound prepared in Example 15 according to the procedure described in the example 17, to give 51 mg (yield: 35%) of the target compound.
$^1$H NMR (200 MHz, CDCl$_3$) δ1.42(s, 3H), 3.60(s, 3H), 3.65(s, 3H), 4.43(s, 1H), 4.83(d, 1H), 6.19(m, 1H), 6.26(d, 1H), 6.60(dd, 1H), 6.78(d, 1H), 7.30(s, 1H), 7.40(d, 1H), 7.92(dd, 1H)

Example 29

Preparation of (2R,3R,4S)-6-amino-3,4-dihydro-3-hydroxy-2-dimethoxymethyl-2-methyl-4-(4-methoxycarbonyl-2-thioxobenzoxazol-3-yl)-2H-1-benzopyran Reaction was performed with 117 mg (0.24 mmol) of the compound prepared in Example 14 according to the procedure described in the example 17, to give 83 mg (yield: 75%) of the target compound.
$^1$H NMR (200 MHz, CDCl$_3$) δ1.29(s, 3H), 3.54(s, 3H), 3.66(s, 3H), 3.93(s, 3H), 4.41(s, 1H), 5.29(d, 1H), 6.39(d, 1H), 6.58(t, 1H), 6.71(m, 1H), 7.26(m, 2H), 7.47(d, 1H), 7.69(dd, 1H)

Example 30

Preparation of (2R,3R,4S)-6-amino-3,4-dihydro-3-hydroxy-2-dimethoxymethyl-2-methyl-4-(5-trifluoromethyl-2-thioxobenzoxazol-3-yl)-2H-1-benzopyran Reaction was performed with 100 mg (0.2 mmol) of the compound prepared in Example 16 according to the procedure described in the example 17, to give 78 mg (yield: 85%) of the target compound.
$^1$H NMR (200 MHz, CDCl$_3$) δ1.41(s, 3H), 3.51(s, 1H), 3.59(s, 3H), 3.64(s, 3H), 4.42(s, 1H), 4.77(d, 1H), 6.22(d, 1H), 6.27(d, 1H), 6.60(dd, 1H), 6.81(m, 2H), 7.46(m, 2H)

Example 31

Preparation of (2R,3R,4S)-6-nitro-3,4-dihydro-3-acetoxy-2-dimethoxymethyl-2-methyl-4-(2-thioxobenzoxazol-3-yl)-2H-1-benzopyran 200 mg (0.46 mmol) of the compound obtained in Example 1 was dissolved in 2 ml of dichloromethane, to which 87 μl (0.93 mmol) of acetic anhydride, 0.13 ml (0.93 mmol) of triethylamine and 17 mg (0.14 mmol) of 4-dimethylaminopyridine were added in that order. The reaction was stirred for 2 hours at room temperature, 10 ml of saturated NaHCO$_3$ solution was added and extraction was performed with 30 ml of dichloromethane. The extract was washed with brine and dried over anhydrous MgSO4, and concentrated under reduced pressure. The residue was purified by silica gel column chromatography (hexane:ethyl acetate=2:1), to give 211 mg (yield: 97%) of the target compound.
$^1$H NMR (200 MHz, CDCl$_3$) δ1.56(s, 3H), 2.02(s, 3H), 3.54(s, 3H), 3.60(s, 3H), 4.34(s, 1H), 5.96(d, 1H), 6.39(d, 1H), 6.59(d, 1H), 7.06(m, 1H), 7.16-7.25(m, 2H), 7.38(d, 1H), 7.79(d, 1H), 8.17(dd, 1H)

Example 32

Preparation of (2R,3R,4S)-6-amino-3,4-dihydro-3-acetoxy-2-dimethoxymethyl-2-methyl-4-(2-thioxobenzoxazol-3-yl)-2H-1-benzopyran Reaction was performed with 106 mg (0.22 mmol) of the compound prepared in Example 31 according to the procedure described in the example 17, to give 85 mg (yield: 87%) of the target compound.
$^1$H NMR (200 MHz, CDCl$_3$) δ1.46(s, 3H), 2.01(s, 3H), 3.52(s, 3H), 3.56(s, 3H), 4.28(s, 1H), 5.89(d, 1H), 6.21(d, 1H), 6.38(d, 1H), 6.61(m, 2H), 6.88(d, 1H), 7.07(m, 1H), 7.18(m, 1H), 7.33(dd, 1H)

Example 33

Preparation of (2R,3R,4S)-6-acetylamino-3,4-dihydro-3-hydroxy-2-dimethoxymethyl-2-methyl-4-(2-thioxobenzoxazol-3-yl)-2H-1-benzopyran 100 mg (0.25 mmol) of the compound obtained in Example 17 was dissolved in 2 ml of dichloromethane, to which 23 μl (0.25 mmol) of acetic anhydride, 52 μl (0.37 mmol) of triethylamine and 9.1 mg (0.07 mmol) of 4-dimethylaminopyridine were added in that order. The reaction was stirred for 3 hours at room temperature, 10 ml of saturated NaHCO$_3$ solution was added and extraction was performed with 40 ml of dichloromethane. The extract was washed with brine and dried over anhydrous MgSO4, and concentrated under reduced pressure. The residue was purified by silica gel column chromatography (hexane:ethyl acetate=2:1), to give 96 mg (yield: 86%) of the target compound.
$^1$H NMR (200 MHz, CDCl$_3$) δ1.45(s, 3H), 2.02(s, 3H), 3.51(s, 1H), 3.61(s, 3H), 3.64(s, 3H), 4.45(s, 1H), 4.79(d, 1H), 6.35(d, 1H), 6.55(d, 1H), 6.63(d, 1H), 6.94(d, 1H), 7.02-7.22(m, 2H), 7.32(d, 1H), 7.76(dd, 1H)

Example 34

Preparation of (2R,3R,4S)-6-acetylamino-3,4-dihydro-3-acetoxy-2-dimethoxymethyl-2-methyl-4-(2-thioxobenzoxazol-3-yl)-2H-1-benzopyran Reaction was performed with 100 mg (0.25 mmol) of the compound prepared in the example 17, 76 μl (0.75 mmol) of acetic anhydride, 104 μl (0.75 mmol) of triethylamine and 9 mg (0.07 mmol) of 4-dimethylaminopyridine according to the procedure described in Example 33, to give 113 mg (yield: 93%) of the target compound.

¹H NMR (200 MHz, CDCl₃) δ1.48(s, 3H), 2.00(s, 3H), 2.02(s, 3H), 3.52(s, 3H), 3.57(s, 3H), 4.30(s, 1H), 5.92(d, 1H), 6.44(d, 1H), 6.53(d, 1H), 6.68(d, 1H), 7.00-7.22(m, 3H), 7.29(m, 1H), 7.73(dd, 1H)

Example 35

Preparation of (2R,3R,4S)-6-benzoylamino-3,4-dihydro-3-hydroxy-2-dimethoxymethyl-2-methyl-4-(2-thioxobenzoxazol-3-yl)-2H-1-benzopyran 80 mg (0.20 mmol) of the compound obtained in Example 17 was dissolved in 1 ml of tetrahydropurane, to which 23 µl (0.20 mmol) of benzoil chloride and 42 µl (0.30 mmol) of triethylamine were added. They were reacted at room temperature for 1 hour. Then, 10 ml of saturated NaHCO₃ solution was added and extraction was performed with 30 ml of ethyl acetate. Organic layer was washed with brine and dried over anhydrous MgSO4, and concentrated under reduced pressure. The residue was purified by silica gel column chromatography (hexane:ethyl acetate=2:1), to give 93 mg (yield: 92%) of the target compound.

¹H NMR (200 MHz, CDCl₃) δ1.47(s, 3H), 3.51(br-s, 1H), 3.62(s, 3H), 3.65(s, 3H), 4.46(s, 1H), 4.82(d, 1H), 6.40(d, 1H), 6.58(d, 1H), 6.77(s, 1H), 7.01(d, 1H), 7.07(t, 1H), 7.18(t, 1H), 7.32-7.49(m, 3H), 7.70-7.76(m, 2H), 7.95(d, 1H)

Example 36

Preparation of (2R,3R,4S)-6-trifluoroacetylamino-3,4-dihydro-3-hydroxy-2-dimethoxymethyl-2-methyl-4-(2-thioxobenzoxazol-3-yl)-2H-1-benzopyran Reaction was performed with 80 mg (0.20 mmol) of the compound prepared in the example 17 and 28 µl (0.20 mmol) of trifluoroacetic anhydride according to the procedure described in Example 33, to give 94 mg (yield: 94%) of the target compound.

¹H NMR (300 MHz, CDCl₃) δ1.47(s, 3H), 3.50(br-s, 1H), 3.61(s, 3H), 3.65(s, 3H), 4.46(s, 1H), 4.83(d, 1H), 6.40(d, 1H), 6.54(d, 1H), 6.79(d, 1H), 7.02(d, 1H), 7.09(dd, 1H), 7.21(dd, 1H), 7.38(d, 1H), 7.77(dd, 1H)

Example 37

Preparation of (2R,3R,4S)-6-methanesulfonylamino-3,4-dihydro-3-hydroxy-2-dimethoxymethyl-2-methyl-4-(2-thioxobenzoxazol-3-yl)-2H-1-benzopyran 90 mg (0.22 mmol) of the compound prepared in Example 17 was dissolved in 1 ml of dichloromethane, to which 58 µl (0.34 mmol) of methanesulfonyl chloride and 17 µl (0.22 mmol) of diaisopropylethylamine were added. The reaction was stirred for 10 hours at room temperature, 67 mg (yield: 64%) of the target compound was obtained through reaction accomplished by the same procedure as used in Example 33.

¹H NMR (300 MHz, CDCl₃) δ1.49(s, 3H), 2.68(s, 3H), 3.50(s, 1H), 3.60(s, 3H), 3.64(s, 3H), 4.46(s, 1H), 4.78(d, 1H), 6.07(s, 1H), 6.40(d, 1H), 6.47(d, 1H), 6.60(d, 1H), 6.99(d, 1H), 7.08(dd, 1H), 7.20(dd, 1H), 7.29-7.39(m, 2H)

Example 38

Preparation of (2R,3R,4S)-6-nitro-3,4-dihydro-3-hydroxy-2-methoxymethyl-2-methyl-4-(2-thioxobenzoxazol-3-yl)-2H-1-benzopyran <Step 1> Preparation of (2R,3R,4S)-6-nitro-3,4-dihydro-3-hydroxy-2-methoxymethyl-2-methyl-4-[(2-hydroxyphenyl)amino]-2H-1-benzopyran Reaction was performed with 200 mg (0.79 mmol) of epoxide compound (2R,3R,4R)-6-nitro-3,4-dihydro-3,4-epoxy-2-methoxymethyl-2-methyl-2H-1-benzopyran and 213 mg (0.95 mmol) of 2-aminophenol according to the procedure described in the step 1 of the example 1, to give 190 mg (yield: 67%) of the target compound.

¹H NMR (300 MHz, CDCl₃) δ1.31(s, 3H), 3.48(s, 3H), 3.62(d, 1H), 3.73(d, 1H), 4.12(d, 1H), 4.16(br-t, 1H), 4.50(br-t, 1H), 6.72-6.92(m, 5H), 8.03(dd, 1H), 8.34(d, 1H)

<Step 2> Preparation of (2R,3R,4S)-6-nitro-3,4-dihydro-3-hydroxy-2-methoxymethyl-2-methyl-4-(2-thioxobenzoxazol-3-yl)-2H-1-benzopyran Reaction was performed with 120 mg (0.30 mmol) of the compound prepared in the above step 1 according to the procedure described in the step 2 of the example 1, to give 110 mg (yield: 87%) of the target compound.

¹H NMR (300 MHz, CDCl₃) δ1.44(s, 3H), 2.95(d, 1H), 3.46(s, 3H), 3.68(d, 1H), 3.74(d, 1H), 4.76(dd, 1H), 6.36(d, 1H), 6.57(d, 1H), 7.05-7.41(m, 4H), 7.77(d, 1H), 8.14(dd, 1H)

Example 39

Preparation of (2R,3R,4S)-6-nitro-3,4-dihydro-3-hydroxy-2-methoxymethyl-2-methyl-4-(5-chloro-2-thioxobenzoxazol-3-yl)-2H-1-benzopyran <Step 1> Preparation of (2R,3R,4S)-6-nitro-3,4-dihydro-3-hydroxy-2-methoxymethyl-2-methyl-4-[(5-chloro-2-hydroxyphenyl)amino]-2H-1-benzopyran Reaction was performed with 400 mg (1.59 mmol) of epoxide compound (2R,3R,4R)-6-nitro-3,4-dihydro-3,4-epoxy-2-methoxymethyl-2-methyl-2H-1-benzopyran and 390 mg (1.74 mmol) of 4-chloro-2-aminophenol according to the procedure described in the step 1 of the example 1, to give 300 mg (yield: 48%) of the target compound.

¹H NMR (300 MHz, CDCl₃) δ1.34(s, 3H), 3.49(s, 3H), 3.62(d, 1H), 3.74(d, 1H), 4.15(d, 1H), 4.50(d, 1H), 6.61-6.69 (m, 2H), 6.81(s, 1H), 6.91(d, 1H), 8.02(dd, 1H), 8.23(d, 1H)

<Step 2> Preparation of (2R,3R,4S)-6-nitro-3,4-dihydro-3-hydroxy-2-methoxymethyl-2-methyl-4-(5-chloro-2-thioxobenzoxazol-3-yl)-2H-1-benzopyran Reaction was performed with 120 mg (0.30 mmol) of the compound prepared in the above step 1 according to the procedure described in the step 2 of the example 1, to give 90 mg (yield: 67%) of the target compound.

¹H NMR (300 MHz, CDCl₃) δ1.44(s, 3H), 2.95(br-s, 1H), 3.47(s, 3H), 3.68(d,1H), 3.72(dd, 2H), 4.69(d, 1H), 6.34(d, 1H), 6.53(d, 1H), 7.11-7.35(m, 3H), 7.76(d, 1H), 8.17(dd, 1H)

Example 40

Preparation of (2R,3R,4S)-6-nitro-3,4-dihydro-3-hydroxy-2-methoxycarbonyl-2-methyl-4-(2-thioxobenzoxazol-3-yl)-2H-1-benzopyran <step 1> Preparation of (2R,3R,4S)-6-nitro-3,4-dihydro-3-hydroxy-2-methoxycarbonyl-2-methyl-4-[(2-hydroxyphenyl)amino]-2H-1-benzopyran Reaction was performed with 200 mg (0.75 mmol) of epoxide compound (2R,3R,4R)-6-nitro-3,4-dihydro-3,4-epoxy-2-methoxycarbonyl-2-methyl-2H-1-benzopyran and 81 mg (0.74 mmol) of 2-aminophenol according to the procedure described in the step 1 of the example 1, to give 275 mg (yield: 95%) of the target compound.
$^1$H NMR (300 MHz, CDCl$_3$) δ1.72(s, 3H), 2.36(br-s, 1H), 3.55(s, 3H), 4.35(d, 1H), 4.43(d, 1H), 5.60(br-s, 1H), 6.38(d, 1H), 6.55(t, 1H), 6.66(d, 1H), 6.76(m, 1H), 7.01(d, 1H), 7.80(dd, 1H), 8.34(d, 1H)

<step 2> Preparation of (2R,3R,4S)-6-nitro-3,4-dihydro-3-hydroxy-2-methoxycarbonyl-2-methyl-4-(2-thioxobenzoxazol-3-yl)-2H-1-benzopyran Reaction was performed with 120 mg (0.32 mmol) of the compound prepared in the above step 1 according to the procedure described in the step 2 of the example 1, to give 95 mg (yield: 71%) of the target compound.
$^1$H NMR (300 MHz, CDCl$_3$) δ1.76(s, 3H), 3.32(br-s, 1H), 3.84(s, 3H), 4.88(d, 1H), 6.31(d, 1H), 6.53(d, 1H), 7.05-7.27 (m, 3H), 7.43(d, 1H), 7.83(d, 1H), 8.20(dd, 1H)

Example 41

Preparation of (2R,3R,4S)-6-nitro-3,4-dihydro-3-hydroxy-2-methoxycarbonyl-2-methyl-4-(5-chloro-2-thioxobenzoxazol-3-yl)-2H-1-benzopyran <Step 1> Preparation of (2R,3R,4S)-6-nitro-3,4-dihydro-3-hydroxy-2-methoxycarbonyl-2-methyl-4-(5-chloro-2-hydroxyphenyl)amino]-2H-1-benzopyran Reaction was performed with 100 mg (0.40 mmol) of epoxide compound (2R,3R,4R)-6-nitro-3,4-dihydro-3,4-epoxy-2-methoxycarbonyl-2-methyl-2H-1-benzopyran and 99 mg (0.44 mmol) of 4-chloro-2-aminophenol according to the procedure described in the step 1 of the example 1, to give 150 mg (yield: 95%) of the target compound.
$^1$H NMR (300 MHz, CDCl$_3$) δ1.73(s, 3H), 2.70(br-s, 1H), 3.52(s, 3H), 4.36(d, 1H), 4.38(d, 1H), 5.87(br-s, 1H), 6.26(d, 1H), 6.49(d, 1H), 6.50(s, 1H), 6.99(d, 1H), 7.81(dd, 1H), 8.34(d, 1H)

<Step 2> Preparation of (2R,3R,4S)-6-nitro-3,4-dihydro-3-hydroxy-2-methoxycarbonyl-2-methyl-4-(5-chloro-2-thioxobenzoxazol-3-yl)-2H-1-benzopyran Reaction was performed with 60 mg (0.14 mmol) of the compound prepared in the above step 1 according to the procedure described in the step 2 of the example 1, to give 65 mg (yield: 98%) of the target compound.
$^1$H NMR (200 MHz, CDCl$_3$) δ1.73(s, 3H), 3.40(d, 1H), 3.88(s, 3H), 4.80(dd, 1H), 6.29(s, 1H), 6.50(d, 1H), 7.15-7.36 (m, 3H), 7.80(d, 1H), 8.20(dd, 1H)

Example 42

Preparation of (2R,3R,4S)-6-nitro-3,4-dihydro-3-hydroxy-2-([1,3]dioxolan-2-yl)-2-methyl-4-(2-thioxobenzoxazol-3-yl)-2H-1-benzopyran <Step 1> Preparation of (2R,3R,4S)-6-nitro-3,4-dihydro-3-hydroxy-2-([1,3]dioxolan-2-yl)-2-methyl-4-[(2-hydroxyphenyl)amino]-2H-1-benzopyran Reaction was performed with 900 mg (3.22 mmol) of epoxide compound (2R,3R,4R)-6-nitro-3,4-dihydro-3,4-([1,3]dioxolan-2-yl)-2-methyl-2H-1-benzopyran and 352 mg (3.22 mmol) of 2-aminophenol according to the procedure described in the step 1 of the example 1, to give 965 mg (yield: 77%) of the target compound.
$^1$H NMR (300 MHz, CDCl$_3$) δ1.41(s, 3H), 3.57(br-s, 1H), 4.03(m, 6H), 4.51(d, 1H), 5.41(s, 1H), 6.76(m, 4H), 6.95(d, 1H), 8.04(dd, 1H), 8.38(d, 1H) Mass: 388, 258, 190, 129, 109, 73

<Step 2> Preparation of (2R,3R,4S)-6-nitro-3,4-dihydro-3-hydroxy-2-([1,3]dioxolan-2-yl)-2-methyl-4-(2-thioxobenzoxazol-3-yl)-2H-1-benzopyran Reaction was performed with 300 mg (0.77 mmol) of the compound prepared in the above step 1 according to the procedure described in the step 2 of the example 1, to give 193 mg (yield: 58%) of the target compound.
$^1$H NMR (300 MHz, CDCl$_3$) δ1.55(s, 3H), 3.20(d, 1H), 4.10(m, 4H), 4.77(dd, 1H), 5.16(s, 1H), 6.40(d, 1H), 6.55(d, 1H), 7.06(t, 1H), 7.09(d, 1H), 7.13(t, 1H), 7.42(d, 1H), 7.79 (d, 1H), 8.02(dd, 1H) Mass: 430, 412, 339, 190, 73

Example 43

Preparation of (2R,3R,4S)-6-nitro-3,4-dihydro-3-hydroxy-2-([1,3]dioxan-2-yl)-2-methyl-4-(2-thioxobenzoxazol-3-yl)-2H-1-benzopyran <Step 1> Preparation of (2R,3R,4S)-6-nitro-3,4-dihydro-3-hydroxy-2-([1,3]dioxan-2-yl)-2-methyl-4-[(2-hydroxyphenyl)amino]-2H-1-benzopyran Reaction was performed with 600 mg (2.05 mmol) of epoxide compound (2R,3R,4R)-6-nitro-3,4-dihydro-3,4-([1,3]dioxolan-2-yl)-2-methyl-2H-1-benzopyran and 668 mg (2.05 mmol) of 2-aminophenol according to the procedure described in the step 1 of the example 1, to give 668 mg (yield: 81%) of the target compound.
$^1$H NMR (300 MHz, CDCl$_3$) δ1.38(s, 3H), 1.49(d, 1H), 2.15(m, 1H), 3.95(m, 3H), 4.08(d, 1H), 4.33(m, 3H), 4.40(t, 1H), 4.79(s, 1H), 6.84(m, 4H), 6.97(d, 1H), 8.06(dd, 1H), 8.60(d, 1H) Mass: 402, 258, 190, 143, 109, 87

<Step 2> Preparation of (2R,3R,4S)-6-nitro-3,4-dihydro-3-hydroxy-2-([1,3]dioxan-2-yl)-2-methyl-4-(2-thioxobenzoxazol-3-yl)-2H-1-benzopyran Reaction was performed with 150 mg (0.37 mmol) of the compound prepared in the above step 1 according to the procedure described in the step 2 of the example 1, to give 138 mg (yield: 84%) of the target compound.
$^1$H NMR (300 MHz, CDCl$_3$) δ1.50(d, 1H), 2.04(s, 3H), 2.20(m, 1H), 3.92(m, 2H), 4.20(dd, 1H), 4.30(dd, 1H), 4.87 (s, 1H), 5.32(d, 1H), 6.45(d, 1H), 6.52(d, 1H), 7.08(t, 1H), 7.23(m, 2H), 7.42(d, 1H), 7.72(d, 1H), 8.14(dd, 1H) Mass: 444, 426, 206, 160, 87

Example 44

Preparation of (2R,3R,4S)-6-nitro-3,4-dihydro-3-hydroxy-2-diethoxymethyl-2-methyl-4-(2-thioxobenzoxazol-3-yl)-2H-1-benzopyran <Step 1> Preparation of (2R,3R,4S)-6-nitro-3,4-dihydro-3-hydroxy-2-diethoxymethyl-2-methyl-4-[(2-hydroxyphenyl)amino]-2H-1-benzopyran Reaction was performed with 818 mg (2.64 mmol) of epoxide compound (2R,3R,4R)-6-nitro-3,4-dihydro-3,4-epoxy-2-diethoxymethyl-2-methyl-2H-1-benzopyran and 289 mg (2.64 mmol) of 2-aminophenol according to the procedure described in the step 1 of the example 1, to give 833 mg (yield: 75%) of the target compound.

$^1$H NMR (300 MHz, CDCl$_3$) δ1.26(m, 6H), 1.38(s, 3H), 3.72(m, 2H), 3.89(m, 2H), 3.92(d, 1H), 4.08(s, 1H), 4.26(d, 1H), 4.40(dd, 1H), 4.57(s, 1H), 6.43(s, 1H), 6.82-6.92(m, 5H), 8.06(dd, 1H), 8.50(d, 1H)

<Step 2> Preparation of (2R,3R,4S)-6-nitro-3,4-dihydro-3-hydroxy-2-diethoxymethyl-2-methyl-4-(2-thioxobenzoxazol-3-yl)-2H-1-benzopyran Reaction was performed with 200 mg (0.48 mmol) of the compound prepared in the above step 1 according to the procedure described in the step 2 of the example 1, to give 199 mg (yield: 90%) of the target compound.

$^1$H NMR (300 MHz, CDCl$_3$) δ1.27(t, 6H), 1.55(s, 3H), 3.73(m, 3H), 3.92(m, 2H), 4.65(s, 1H), 4.88(d, 1H), 6.41(d, 1H), 6.51(d, 1H), 7.05(m, 2H), 7.22(dd, 1H), 7.42(d, 1H), 7.79(d, 1H), 8.14(dd, 1H)

Example 45

Preparation of (2R,3S,4R)-6-nitro-3,4-dihydro-3-hydroxy-2-diethoxymethyl-2-methyl-4-(2-thioxobenzoxazol-3-yl)-2H-1-benzopyran <Step 1> Preparation of (2R,3S,4R)-6-nitro-3,4-dihydro-3-hydroxy-2-diethoxymethyl-2-methyl-4-[(2-hydroxyphenyl)amino]-2H-1-benzopyran Reaction was performed with 1.1 g (3.54 mmol) of epoxide compound (2R,3S,4S)-6-nitro-3,4-dihydro-3,4-epoxy-2-diethoxymethyl-2-methyl-2H-1-benzopyran and 387 mg (3.54 mmol) of 2-aminophenol according to the procedure described in the step 1 of the example 1, to give 1.15 g (yield: 78%) of the target compound.

$^1$H NMR (300 MHz, CDCl$_3$) δ1.07(t, 3H), 1.24(t, 3H), 1.54(s, 3H), 3.58(m, 2H), 3.80(m, 2H), 4.03(dd, 1H), 4.16(d, 1H), 4.31(d, 1H), 4.60(m, 2H), 5.78(br-s, 1H), 6.72-6.87(m, 4H), 6.91(d, 1H), 8.08(dd, 1H), 8.42(d, 1H)

<Step 2> Preparation of (2R,3S,4R)-6-nitro-3,4-dihydro-3-hydroxy-2-diethoxymethyl-2-methyl-4-(2-thioxobenzoxazol-3-yl)-2H-1-benzopyran Reaction was performed with 200 mg (0.48 mmol) of the compound prepared in the above step 1 according to the procedure described in the step 2 of the example 1, to give 169 mg (yield: 77%) of the target compound.

$^1$H NMR (300 MHz, CDCl$_3$) δ0.84(t, 3H), 1.14(t, 3H), 1.68(s, 3H), 3.61(m, 3H), 3.78(m, 1H), 3.87(m, 1H), 4.28(dd, 1H), 4.75(s, 1H), 6.33(d, 1H), 6.79(d, 1H), 7.03(dd, 1H), 7.06(d, 1H), 7.21(dd, 1H), 7.42(d, 1H), 7.76(d, 1H), 8.16(dd, 1H) Mass: 460(M+)

Example 46

Preparation of (2S,3R,4S)-6-nitro-3,4-dihydro-3-hydroxy-2-diethoxymethyl-2-methyl-4-(2-thioxobenzoxazol-3-yl)-2H-1-benzopyran <Step 1> Preparation of (2S,3R,4S)-6-nitro-3,4-dihydro-3-hydroxy-2-diethoxymethyl-2-methyl-4-[(2-hydroxyphenyl)amino]-2H-1-benzopyran Reaction was performed with 450 mg (1.45 mmol) of epoxide compound (2S,3R,4R)-6-nitro-3,4-dihydro-3,4-epoxy-2-diethoxymethyl-2-methyl-2H-1-benzopyran and 159 mg (1.45 mmol) of 2-aminophenol according to the procedure described in the step 1 of the example 1, to give 555 mg (yield: 91%) of the target compound.

$^1$H NMR (300 MHz, CDCl$_3$) δ1.07(t, 3H), 1.24(t, 3H), 1.54(s, 3H), 3.58(m, 2H), 3.80(m, 2H), 4.03(dd, 1H), 4.16(d, 1H), 4.31(d, 1H), 4.60(m, 2H), 5.78(br-s, 1H), 6.72-6.87(m, 4H), 6.91(d, 1H), 8.08(dd, 1H), 8.42(d, 1H)

<Step 2> Preparation of (2S,3R,4S)-6-nitro-3,4-dihydro-3-hydroxy-2-diethoxymethyl-2-methyl-4-(2-thioxobenzoxazol-3-yl)-2H-1-benzopyran Reaction was performed with 180 mg (0.43 mmol) of the compound prepared in the above step 1 according to the procedure described in the step 2 of the example 1, to give 159 mg (yield: 80%) of the target compound.

$^1$H NMR (300 MHz, CDCl$_3$) δ0.84(t, 3H), 1.14(t, 3H), 1.68(s, 3H), 3.61(m, 3H), 3.78(m, 1H), 3.87(m, 1H), 4.28(dd, 1H), 4.75(s, 1H), 6.33(d, 1H), 6.79(d, 1H), 7.03(dd, 1H), 7.06(d, 1H), 7.21(dd, 1H), 7.42(d, 1H), 7.76(d, 1H), 8.16(dd, 1H) Mass: 460(M+)

Example 47

Preparation of (2S,3S,4R)-6-nitro-3,4-dihydro-3-hydroxy-2-diethoxymethyl-2-methyl-4-(2-thioxobenzoxazol-3-yl)-2H-1-benzopyran <Step 1> Preparation of (2S,3S,4R)-6-nitro-3,4-dihydro-3-hydroxy-2-diethoxymethyl-2-methyl-4-[(2-hydroxyphenyl)amino]-2H-1-benzopyran Reaction was performed with 346 mg (1.12 mmol) of epoxide compound (2S,3S,4S)-6-nitro-3,4-dihydro-3,4-epoxy-2-diethoxymethyl-2-methyl-2H-1-benzopyran and 122 mg (1.12 mmol) of 2-aminophenol according to the procedure described in the step 1 of the example 1, to give 416 mg (yield: 89%) of the target compound.

$^1$H NMR (300 MHz, CDCl$_3$) δ1.26(m, 6H), 1.38(s, 3H), 3.72(m, 2H), 3.89(m, 2H), 3.92(d, 1H), 4.08(s, 1H), 4.26(d, 1H), 4.40(dd, 1H), 4.57(s, 1H), 6.43(s, 1H), 6.82-6.92(m, 5H), 8.06(dd, 1H), 8.50(d, 1H)

<Step 2> Preparation of (2S,3S,4R)-6-nitro-3,4-dihydro-3-hydroxy-2-diethoxymethyl-2-methyl-4-(2-thioxobenzoxazol-3-yl)-2H-1-benzopyran Reaction was performed with 130 mg (0.31 mmol) of the compound prepared in the above step 1 according to the procedure described in the step 2 of the example 1, to give 125 mg (yield: 87%) of the target compound.

$^1$H NMR (300 MHz, CDCl$_3$) δ1.27(t, 6H), 1.55(s, 3H), 3.73(m, 3H), 3.92(m, 2H), 4.65(s, 1H), 4.88(d, 1H), 6.41(d,

1H), 6.51(d, 1H), 7.05(m, 2H), 7.22(dd, 1H), 7.42(d, 1H), 7.79(d, 1H), 8.14(dd, 1H) Mass: 460(M+)

Example 48

Preparation of (2S,3R,4S)-6-amino-3,4-dihydro-3-hydroxy-2-diethoxymethyl-2-methyl-4-(2-thioxobenzoxazol-3-yl)-2H-1-benzopyran Reaction was performed with 200 mg (0.43 mmol) of the compound prepared in Example 46 according to the procedure described in the example 17, to give 177 mg (yield: 95%) of the target compound.

$^1$H NMR (300 MHz, CDCl$_3$) δ0.84(t, 3H), 1.14(t, 3H), 1.68(s,3H), 3.61(m, 3H), 3.78(m, 1H), 3.87(m, 1H), 4.28(dd, 1H), 4.75(s, 1H), 6.33(d, 1H), 6.79(d, 1H), 7.03(dd, 1H), 7.06(d, 1H), 6.78(d,1H), 7.02-7.22(m, 2H), 7.35(dd, 1H) Mass: 430(M+)

The following experiments were performed to investigate pharmacological activities of compounds of the present invention represented in <Formula 1>.

Experimental Example 1

Cardioprotective Effect on Isolated Ischemic Heart Models of White Rats

The experiment confirming whether the compounds of <Formula 1> had the protective effect (antiischemic effect) on ischemic heart was accomplished in the below.

100 mg/kg of sodium pentobarbital was injected in abdominal cavity of white male rats (300~450 g, obtained form the experimental animal team of the Korea Research Institute of Chemical Technology) to anesthetize them. Then, an intravenous injection of 1000 U/kg of heparin was performed before taking out heart. Particularly, cannula(PE 240) was inserted in the trachea, and artificial respiration was tried upon the rat by using a rodent ventilator. Under that condition, aortic cannula was inserted in the aorta and heart was taken out under retrograde perfusion. The extracted heart was hung on Langendorff apparatus quickly and unnecessary tissues on heart were removed. Perfusion was induced under static pressure (85 mmHg) with 37° C. modified Krebs-Henseleit bicarbonate buffer (composition <mM/L>: 116 NaCl, 4.7 KCl, 1.1 MgSO$_4$, 1.17 KH$_2$PO$_4$, 24.9 NaHCO$_3$, 2.52 CaCl$_2$, 8.32 Glucose, 2.0 Pyruvate) saturated with 95% O$_2$/5% CO$_2$. A metal cannula, to which a latex balloon filled with an ethanol-distilled water mixture (1:1 vol/vol) was linked, was inserted in left ventricle through pulmonary vein. Then, left ventricular pressure transmitted through the balloon was transduced by using pressure transducer, and amplified by using Plugsys bridge amplifier isovolumetrically. Then, the pressure was recorded in a recorder (Linearcorder mark 8 WR 3500). Thereafter, heart was stabilized for 15 minutes. Then, left ventricular end diastolic pressure (LVEDP) was given by 5 mmHg and such volume of the balloon was kept all through the experiments.

Baseline cardiac contractile function, heart rate (HR), and coronary flow (CF) were measured. Cardiac contractile function was calculated by subtracting LVSP (left ventricular peak systolic pressure) from LVEDP (left ventricular end diastolic pressure), yielding LVDP (left ventricular developed pressure). Double product RPP (rate-pressure product) (DP), another important parameter for indirectly assessing cardiac performance in Langendorff heart, whose cardiac output could not be measured ordinarily, was calculated by multiplying HR by LVDP. Throughout the experiment, total coronary blood flow was measured by the use of coronary flow probe (diameter: 1.0 mm) installed in aortic cannula with electromagnetic flowmeter. Temperature of heart was steadily maintained by immersing the heart at 37° C. in physiological saline solution to which 95% O$_2$/5% CO$_2$ was constantly supplied. After stabilization for 15 min, the hearts were pre-treated for 10 min with vehicle (0.04% DMSO) only or a compound of the present invention or the control material in the vehicle. Thereafter, cardiac contractile function, HR and CF were repeatedly measured. Global ischemia was induced by completely shutting off the perfusate for 30 min. Severity of ischemia was determined as the time to contracture (TTC, min) during global ischemia in which the first 5 mmHg increase in EDP was observed. Then, the hearts were reperfused and, 30 min later, contractile functions (LVDP, HR and CF) were repeatedly measured. After reperfusion was accomplished for 30 min, LDH (lactate dehydrogenase) was measured with a kit as a sensitive index for loss of cell viability. The results were shown in Table 1.

TABLE 1

Cardioprotective activity to isolated ischemic heart

| Compound | Cardioprotective activity to ischemic heart isolated from white rat (10 μM) | | | |
|---|---|---|---|---|
| | LVDP × HR[1] (%) | EDP[2] (mmHg) | TTC[3] (minute) | LDH[4] (unit/g) |
| Vehicle | 15.8 | 45.1 | 19.8 | 31.3 |
| BMS-180448 | 67.6 | 16.5 | 27.8 | 17.2 |
| Compound of example 1 | 53.8 | 19.8 | 25.3 | 4.6 |
| Compound of example 2 | 57.6 | 29.3 | 24.4 | 17.9 |
| Compound of example 3 | 66.8 | 15.3 | 26.6 | 12.6 |
| Compound of example 5 | 47.4 | 21.0 | 29.0 | 20.2 |
| Compound of example 6 | 74.3 | 6.3 | 26.7 | 9.6 |
| Compound of example 7 | 59.4 | 23.3 | 25.6 | 21.1 |
| Compound of example 9 | 61.1 | 27.0 | 23.5 | 30.1 |
| Compound of example 10 | 54.2 | 36.7 | 24.4 | 17.3 |
| Compound of example 16 | 79.3 | 13.3 | 26.5 | na[5] |
| Compound of example 20 | 42.0 | 43.3 | 21.3 | 3.9 |
| Compound of example 36 | 48.4 | 27.3 | 24.9 | na[5] |

[1]left ventricular developed pressure × heart rate
[2]left ventricular end diastolic pressure
[3]time to induce contraction
[4]concentration of lactate dehydogenase
[5]not assayed In vehicle-treated group, reperfusion DP (LVDP X HR), a index for contractility function, was decreased to 15.8% of pre-treatment DP, and EDP was increased to 45.1 mmHg from 5 mmHg, and TTC was 19.8 min, and reperfusion LDH release was 31.3 unit/g as shown in the above.

In BMS-180448 treated group, reperfusion contractile function (DP, LVDP×HR) was 67.6% of pre-treatment DP, which was significantly improved compared to the vehicle treated group. EDP was 16.5 mmHg, significantly lower than control, and TTC was 27.8 min, prolonged than control, and reperfusion LDH release was 17.2 Unit/g, decreased than control. Then, in BMS-180448 treated group, all parameters showed significant protective effect on ischemic heart.

The compounds of the present invention were compared with those of control groups in cardioprotective activity based on contraction capacity, EDP, TTC, LDH, etc. As a result, the compounds of the invention showed similar or superior cardioprotective effect to BMS-180448. Especially, the compounds prepared in Example 6 and example 16 had 74.3% and 79.3% of myocardial contraction capacity (LVDP×HR) each, which were superior to that of BMS-180448. Thus, those compounds were expected to have excellent protective effect to ischemic heart diseases, supported by other indexes as well. Therefore, the compounds of the present invention can be used as a therapeutic agent for ischemic heart diseases owing to their excellent protective effect on ischemic heart. Besides, the compounds can also be used as a protective agent for ischemic brain and retinal cell damage related to ischemia-reperfusion or for organs for storage.

Experimental Example 2

Cardioprotective Activity in Ischemic Heart Isolated from White Rat

In order to investigate the protective effect of compounds of <Formula 1> according to the present invention for ischemic heart, antiischemic effects on white rat hearts were examined as follows.

75 mg/kg of sodium pentobarbital was injected in abdominal cavity of white male rats (350-450 g, Laboratory Animal Division, Korea Research Institute of Chemical Technology) to anesthetize them. After performing tracheotomy, artificial respiration was induced by 10 ml/kg of stroke volume and 60/min. of heart rate. Cannula was inserted in each of vena fermoralis and aorta fermoralis, through which medicines were administered and blood pressure was measured. In the meantime, since body temperature in a ischemic myocardial injury model was very important factor, directly influencing a result, the temperature of a rat was always kept at 37° C. by using a probe for measuring body temperature inserted in rectum and homeothermic blanket control unit. Mean arterial blood pressure and heart rate (HR) of the rat were measured all through the experiments. Statham P23XL pressure transducer (Grass Ins., MA., USA) was used for measuring blood pressure and ECG/RATE Coupler (Hugo Sachs Electronic, Germany) was used for measuring HR. In addition, all the changes were recorded successively by graphtec linearcorder chart recorder (Graphtec Linearcorder WR 3310, Hugo Sachs Electronic).

According to the method of Selye H, left coronary aorta was occluded as follows. Left thoracotomy was induced. That is, the chest of a rat was a little opened. The right chest of the anesthetized rat was pressurized by the middle finger of left hand, so that the heart was pushed out. The heart was fixed gently by the thumb and the index finger of the left hand. A stitch was carefully put on a part including left anterior descending coronary artery by a suture needle with operating thread (5-0 silk ligature), and the heart was quickly positioned again in thoracic cavity. Then, both ends of operating thread were exposed outside. Both ends of operating thread were passed through PE tube (PE100, 2.5 cm) and left for 20 minutes for stabilization. A vehicle or a medicine was administered through the cannula inserted in femoral vein, which was left for 30 minutes in order for the medicine to work thoroughly. BMS-180448 was used for a control group and the dosage of each test medicine and a control medicine was 0.3 mg/kg each.

PE tube threaded on a string was pushed in the heart and the string near the edge of the tube was pulled by hemostatic pincette to stick PE tube vertically to coronary artery, which was pressurized. 45 minutes later, the coronary artery was occluded. Hemostatic pincette was removed and reperfusion went for 90 minutes.

The coronary artery was reoccluded according to the above method and 2 ml of 1% Evans blue solution was administered by intravenous injection. The white rat was sacrificed by the over-dose of pentobarbital, which was intravenously injected. The heart was taken and right ventricle and both atria were removed. Left ventricle was 5~6 slice cut horizontally from apex, and each slice was weighed. The surface of each slice was inputted in a computer by using Hi-scope, a compact micro vision system, and Image pro plus program, from which both normal blood flow tissue area stained by blue and non-stained area on each slice were measured. The ratio of non-stained area to the gross area of each slice was calculated, by which the weight of each slice was multiplied to calculate AAR (area at risk) of each slice. All the AARs were added up, which was then divided by the total weight of left ventricle, resulting in the percentage of AAR (%) represented in the below <Mathematical Formula 1>.

$AAR\ (\%) = (\text{Sum of } AAR \text{ of each slice})/(\text{Total weight of left ventricle}) \times 100$ <Mathematical Formula 1>

The heart slice was cultivated for 15 minutes in 1% 2,3,5-triphenyltetrazolium chloride(TTC) phosphate buffer (37° C., pH 7.4), then was fixed for 20~24 hours in 10% formalin solution. 2,3,5-triphenyltetrazolium chloride was reduced by dehydrogenase and cofactor 'NADH' in myocardium for being formazan dye. Therefore, normal tissues had brick-red color thereby. On the contrary, infarct zone without dehydrogenase nor cofactor was not brick-red because 2,3,5-triphenyltetrazolium chloride was not reduced.

A normal area and an infarct zone of each slice were determined by investigating the coloring of tissues by 2,3,5-triphenyltetrazolium chloride by taking advantage of the method used for AAR measurement. All the infarct zone of each slice were added up, which was divided by the total weight of AAR or the weight of a whole left ventricle, resulting in IZ (%) represented in the below <Mathematical Formula 2>. In the test models of the invention, the lower IZ (%) was, the stronger the antiischemic effect of a test compound. The results were shown in Table 2.

$IZ\ (\%) = (\text{Sum of infarct zone of each slice})/(\text{Total weight of left ventricle or } AAR) \times 100$ <Mathematical Formula 2>

TABLE 2

| Antiischemic activities of compounds of <Formula 1> | |
|---|---|
| Compound | Antiischemic activity (in vivo test using rats) (0.3 mg/kg) IZ/AAR(%) |
| Vehicle | 58.6 |
| BMS-180448 | 39.1 |
| Compound of Example 1 | 39.6 |
| Compound of Example 6 | 42.5 |
| Compound of Example 10 | 46.6 |

As shown in Table 2, in ischemic myocardial injury models prepared from white rats, myocardial infarction size was significantly decreased by compounds of the present invention. Particularly, myocardial infarction size (IZ/AAR, %) to AAR (area at risk) was 58.6% in a vehicle administered group, suggesting that myocardial injury by ischemia was very serious. Myocardial infarction size to AAR in BMS-180448 administered group was 39.1%, suggesting a significant antiischemic action. And compounds of the present invention were proved to have similar antiischmic effect to the control substance BMS-180448. In particular, the compounds of Example 1 and Example 6 showed not only excellent cardioprotective activity in vitro but also low myocardial infarction sized to AAR, 39.6% and 42.5% each, in vivo, meaning also an excellent cardioprotective activity to ischemia-reperfusion. Therefore, the compounds of the present invention can be effectively used as a therapeutic agent for ischemic heart diseases owing to their excellent cardioprotective effects.

INDUSTRIAL APPLICABILITY

As explained hereinbefore, the compounds of the present invention represented in <Formula 1> were confirmed to have excellent cardioprotective activity against damage by ischemia/reperfusion, in vivo and in vitro as well. Thus, a pharmaceutical composition containing benzopyran derivatives substituted with a thioxobenzoxazole derivative, represented in <Formula 1> or pharmaceutically acceptable salts of the same can be used as a protective or therapeutic agent for ischemia-reperfusion related damage or diseases, that is, the compounds are not only useful for the treatment of ischemic heart diseases such as myocardial infarction, unstable angina pectoris, etc, the protection of heart upon thrombolytics therapy or reperfusion therapy such as PTCA (percutaneous transluminal coronary angioplasty) and CABG (coronary artery bypass graft), and the protection of ischemia-reperfusion related tissues such as nerve cells, brain, retinal cells, storage organs, etc.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A benzopyran compound substituted with a thioxobenzoxazole derivative represented in <Formula 1>:

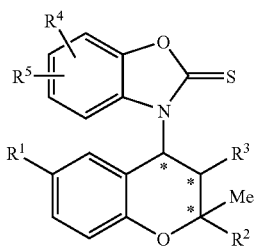

<Formula 1> wherein,
$R^1$ is $NO_2$, $NH_2$, H, CN, $NHCOCH_3$, NHCOPh, $NHCOCF_3$ or $NHSO_2CH_3$;
$R^2$ is

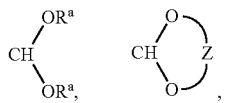

$CH_2OR^a$, $CO_2R^a$ or $R^a$
wherein,
$R^a$ is $C_1$~$C_4$ straight or branched alkyl; and
Z is $C_2$~$C_6$ straight or branched alkyl;
$R^3$ is OH or $OCOCH_3$;
$R^4$ and $R^5$ are independently H, $C_1$~$C_4$ straight or branched alkyl, Cl, Br, F, $NO_2$, OMe, $CO_2Me$ or $CF_3$; and
* represents a chiral carbon,
or a pharmaceutically acceptable salt thereof.

2. The benzopyran compound according to claim 1, substituted with a thioxobenzoxazole derivative selected from the group consisting of:
1) (2R, 3R, 4S)-6-nitro-3,4-dihydro-3-hydroxy-2-dimethoxymethyl-2-methyl-4-(2-thioxobenzoxazol-3-yl)-2H-1-benzopyran;
2) (2R, 3S, 4R)-6-nitro-3,4-dihydro-3-hydroxy-2-dimethoxymethyl-2-methyl-4-(2-thioxobenzoxazol-3-yl)-2H-1-benzopyran;
3) (2S, 3R, 4S)-6-nitro-3,4-dihydro-3-hydroxy-2-dimethoxymethyl-2-methyl-4-(2-thioxobenzoxazol-3-yl)-2H-1-benzopyran;
4) (2S, 3S, 4R)-6-nitro-3,4-dihydro-3-hydroxy-2-dimethoxymethyl-2-methyl-4-(2-thioxobenzoxazol-3-yl)-2H-1-benzopyran;
5) (2R, 3R, 4S)-6-nitro-3,4-dihydro-3-hydroxy-2-dimethoxymethyl-2-methyl-4-(6-methyl-2-thioxobenzoxazol-3-yl)-2H-1-benzopyran;
6) (2R, 3R, 4S)-6-nitro-3,4-dihydro-3-hydroxy-2-dimethoxymethyl-2-methyl-4-(4-methyl-2-thioxobenzoxazol-3-yl)-2H-1-benzopyran;
7) (2R, 3R, 4S)-6-nitro-3,4-dihydro-3-hydroxy-2-dimethoxymethyl-2-methyl-4-(5-chloro-2-thioxobenzoxazol-3-yl)-2H-1-benzopyran;
8) (2R, 3R, 4S)-6-nitro-3,4-dihydro-3-hydroxy-2-dimethoxymethyl-2-methyl-4-(5-methyl-2-thioxobenzoxazol-3-yl)-2H-1-benzopyran;
9) (2R, 3R, 4S)-6-nitro-3,4-dihydro-3-hydroxy-2-dimethoxymethyl-2-methyl-4-(6-nitro-2-thioxobenzoxazole-3-yl)-2H-1-benzopyran;
10) (2R, 3R, 4S)-6-nitro-3,4-dihydro-3-hydroxy-2-dimethoxymethyl-2-methyl-4-(5-methoxy-2-thioxobenzoxazol-3-yl)-2H-1-benzopyran;
11) (2R, 3R, 4S)-6-nitro-3,4-dihydro-3-hydroxy-2-dimethoxymethyl-2-methyl-4-(5-bromo-2-thioxobenzoxazol-3-yl)-2H-1-benzopyran;
12) (2R, 3R, 4S)-6-nitro-3,4-dihydro-3-hydroxy-2-dimethoxymethyl-2-methyl-4-(5-t-butoxy-2-thioxobenzoxazol-3-yl)-2H-1-benzopyran;
13) (2R, 3R, 4S)-6-nitro-3,4-dihydro-3-hydroxy-2-dimethoxymethyl-2-methyl-4-(6-fluoro-2-thioxobenzoxazol-3-yl)-2H-1-benzopyran;
14) (2R, 3R, 4S)-6-nitro-3,4-dihydro-3-hydroxy-2-dimethoxymethyl-2-methyl-4-(4-methoxycarbonyl-2-thioxobenzoxazol-3-yl)-2H-1-benzopyran;
15) (2R, 3R, 4S)-6-nitro-3,4-dihydro-3-hydroxy-2-dimethoxymethyl-2-methyl-4-(5-methoxycarbonyl-2-thioxobenzoxazol-3-yl)-2H-1-benzopyran;
16) (2R, 3R, 4S)-6-nitro-3,4-dihydro-3-hydroxy-2-dimethoxymethyl-2-methyl-4-(5-trifluoromethyl-2-thioxobenzoxazol-3-yl)-2H-1-benzopyran;
17) (2R, 3R, 4S)-6-amino-3,4-dihydro-3-hydroxy-2-dimethoxymethyl-2-methyl-4-(2-thioxobenzoxazol-3-yl)-2H-1-benzopyran;
18) (2S, 3S, 4R)-6-amino-3,4-dihydro-3-hydroxy-2-dimethoxymethyl-2-methyl-4-(2-thioxobenzoxazol-3-yl)-2H-1-benzopyran;

19) (2S, 3R, 4S)-6-amino-3,4-dihydro-3-hydroxy-2-dimethoxymethyl-2-methyl-4-(2-thioxobenzoxazol-3-yl)-2H-1-benzopyran;
20) (2R, 3S, 4R)-6-amino-3,4-dihydro-3-hydroxy-2-dimethoxymethyl-2-methyl-4-(2-thioxobenzoxazol-3-yl)-2H-1-benzopyran;
21) (2R, 3R, 4S)-6-amino-3,4-dihydro-3-hydroxy-2-dimethoxymethyl-2-methyl-4-(6-methyl-2-thioxobenzoxazol-3-yl)-2H-1-benzopyran;
22) (2R, 3R, 4S)-6-amino-3,4-dihydro-3-hydroxy-2-dimethoxymethyl-2-methyl-4-(5-methyl-2-thioxobenzoxazol-3-yl)-2H-1-benzopyran;
23) (2R, 3R, 4S)-6-amino-3,4-dihydro-3-hydroxy-2-dimethoxymethyl-2-methyl-4-(4-methyl-2-thioxobenzoxazol-3-yl)-2H-1-benzopyran;
24) (2R, 3R, 4S)-6-amino-3,4-dihydro-3-hydroxy-2-dimethoxymethyl-2-methyl-4-(5-chloro-2-thioxobenzoxazol-3-yl)-2H-1-benzopyran;
25) (2R, 3R, 4S)-6-amino-3,4-dihydro-3-hydroxy-2-dimethoxymethyl-2-methyl-4-(5-methoxy-2-thioxobenzoxazol-3-yl)-2H-1-benzopyran;
26) (2R, 3R, 4S)-6-amino-3,4-dihydro-3-hydroxy-2-dimethoxymethyl-2-methyl-4-(5-t-butoxy-2-thioxobenzoxazol-3-yl)-2H-1-benzopyran;
27) (2R, 3R, 4S)-6-amino-3,4-dihydro-3-hydroxy-2-dimethoxymethyl-2-methyl-4-(6-fluoro-2-thioxobenzoxazol-3-yl)-2H-1-benzopyran;
28) (2R, 3R, 4S)-6-amino-3,4-dihydro-3-hydroxy-2-dimethoxymethyl-2-methyl-4-(5-methoxycarbonyl-2-thioxobenzoxazol-3-yl)-2H-1-benzopyran;
29) (2R, 3R, 4S)-6-amino-3,4-dihydro-3-hydroxy-2-dimethoxymethyl-2-methyl-4-(4-methoxycarbonyl-2-thioxobenzoxazol-3-yl)-2H-1-benzopyran;
30) (2R, 3R, 4S)-6-amino-3,4-dihydro-3-hydroxy-2-dimethoxymethyl-2-methyl-4-(5-trifluoromethyl-2-thioxobenzoxazol-3-yl)-2H-1-benzopyran;
31) (2R, 3R, 4S)-6-nitro-3,4-dihydro-3-acetoxy-2-dimethoxymethyl-2-methyl-4-(2-thioxobenzoxazol-3-yl)-2H-1-benzopyran;
32) (2R, 3R, 4S)-6-amino-3,4-dihydro-3-acetoxy-2-dimethoxymethyl-2-methyl-4-(2-thioxobenzoxazol-3-yl)-2H-1-benzopyran;
33) (2R, 3R, 4S)-6-acetylamino-3,4-dihydro-3-hydroxy-2-dimethoxymethyl-2-methyl-4-(2-thioxobenzoxazol-3-yl)-2H-1-benzopyran;
34) (2R, 3R, 4S)-6-acetylamino-3,4-dihydro-3-acetoxy-2-dimethoxymethyl-2-methyl-4-(2-thioxobenzoxazol-3-yl)-2H-1-benzopyran;
35) (2R, 3R, 4S)-6-benzoylamino-3,4-dihydro-3-hydroxy-2-dimethoxymethyl-2-methyl-4-(2-thioxobenzoxazol-3-yl)-2H-1-benzopyran;
36) (2R, 3R, 4S)-6-trifluoroacetylamino-3,4-dihydro-3-hydroxy-2-dimethoxymethyl-2-methyl-4-(2-thioxobenzoxazol-3-yl)-2H-1-benzopyran;
37) (2R, 3R, 4S)-6-methanesulfonylamino-3,4-dihydro-3-hydroxy-2-dimethoxymethyl-2-methyl-4-(2-thioxobenzoxazol-3-yl)-2H-1-benzopyran;
38) (2R, 3R, 4S)-6-nitro-3,4-dihydro-3-hydroxy-2-methoxymethyl-2-methyl-4-(2-thioxobenzoxazol-3-yl)-2H-1-benzopyran;
39) (2R, 3R, 4S)-6-nitro-3,4-dihydro-3-hydroxy-2-methoxymethyl-2-methyl-4-(5-chloro-2-thioxobenzoxazol-3-yl)-2H-1-benzopyran;
40) (2R, 3R, 4S)-6-nitro-3,4-dihydro-3-hydroxy-2-methoxycarbonyl-2-methyl-4-(2-thioxobenzoxazol-3-yl)-2H-1-benzopyran;
41) (2R, 3R, 4S)-6-nitro-3,4-dihydro-3-hydroxy-2-methoxycarbonyl-2-methyl-4-(5-chloro-2-thioxobenzoxazol-3-yl)-2H-1-benzopyran;
42) (2R, 3R, 4S)-6-nitro-3,4-dihydro-3-hydroxy-2-([1,3]dioxolan-2-yl)-2-methyl-4-(2-thioxobenzoxazol-3-yl)-2H-1-benzopyran;
43) (2R, 3R, 4S)-6-nitro-3,4-dihydro-3-hydroxy-2-([1,3]dioxan-2-yl)-2-methyl-4-(2-thioxobenzoxazol-3-yl)-2H-1-benzopyran;
44) (2R, 3R, 4S)-6-nitro-3,4-dihydro-3-hydroxy-2-diethoxymethyl-2-methyl-4-(2-thioxobenzoxazol-3-yl)-2H-1-benzopyran;
45) (2R, 3S, 4R)-6-nitro-3,4-dihydro-3-hydroxy-2-diethoxymethyl-2-methyl-4-(2-thioxobenzoxazol-3-yl)-2H-1-benzopyran;
46) (2S, 3R, 4S)-6-nitro-3,4-dihydro-3-hydroxy-2-diethoxymethyl-2-methyl-4-(2-thioxobenzoxazol-3-yl)-2H-1-benzopyran;
47) (2S, 3S, 4R)-6-nitro-3,4-dihydro-3-hydroxy-2-diethoxymethyl-2-methyl-4-(2-thioxobenzoxazol-3-yl)-2H-1-benzopyran; and
48) (2S, 3R, 4S)-6-amino-3,4-dihydro-3-hydroxy-2-diethoxymethyl-2-methyl-4-(2-thioxobenzoxazol-3-yl)-2H-1-benzopyran, or a pharmaceutically acceptable salt thereof

3. A pharmaceutical composition for treating myocardial infarction, unstable angina pectoris or heart failure containing the benzopyran compound according to claim 1 as an effective ingredient.

4. A pharmaceutical composition comprising the benzopyran compound of claim 1 as an effective ingredient.

* * * * *